(12) United States Patent
Chikamatsu et al.

(10) Patent No.: US 8,228,496 B2
(45) Date of Patent: *Jul. 24, 2012

(54) DEFECT INSPECTION METHOD AND DEFECT INSPECTION APPARATUS

(75) Inventors: Shuichi Chikamatsu, Konosu (JP); Minori Noguchi, Joso (JP); Masayuki Ochi, Kamisato (JP); Kenji Aiko, Ninomiya (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/830,204

(22) Filed: Jul. 2, 2010

(65) Prior Publication Data
US 2010/0271627 A1    Oct. 28, 2010

Related U.S. Application Data

(63) Continuation of application No. 12/038,274, filed on Feb. 27, 2008, now Pat. No. 7,847,927.

(30) Foreign Application Priority Data

Feb. 28, 2007 (JP) ................................. 2007-048355
Nov. 22, 2007 (JP) ................................. 2007-302997

(51) Int. Cl.
*G01N 21/00* (2006.01)
(52) U.S. Cl. ................... 356/237.4; 356/237.5
(58) Field of Classification Search .... 356/237.1–237.6; 250/492.1–492.2; 438/16
See application file for complete search history.

(56) References Cited

U.S. PATENT DOCUMENTS

| | | | |
|---|---|---|---|
| 6,411,377 B1 | 6/2002 | Noguchi et al. | |
| 6,731,384 B2 | 5/2004 | Ohshima et al. | |
| 7,253,891 B2 | 8/2007 | Toker et al. | |
| 2004/0156043 A1 | 8/2004 | Toker et al. | |
| 2004/0169849 A1 | 9/2004 | Kimura et al. | |
| 2006/0181698 A1 | 8/2006 | Treves et al. | |

FOREIGN PATENT DOCUMENTS

| | | |
|---|---|---|
| JP | 63-135848 A | 6/1988 |
| JP | 01-117024 A | 5/1989 |
| JP | 5-60527 A | 3/1993 |
| JP | 2000-105203 A | 4/2000 |
| JP | 2001-60607 A | 3/2001 |
| JP | 2001-264264 A | 9/2001 |
| JP | 2002-188999 A | 7/2002 |
| JP | 2004-177284 A | 6/2004 |
| JP | 2006-515676 A | 6/2006 |

OTHER PUBLICATIONS

Japanese Office Action including partial English language translation dated Nov. 29, 2011 (Eight (8) pages).

*Primary Examiner* — Tri T Ton
(74) *Attorney, Agent, or Firm* — Crowell & Moring LLP

(57) ABSTRACT

Provided are a defect inspection apparatus having a large range for receiving light scattering from fine defects while securing a sufficiently large signal strength; and a defect inspection method for the same. The defect inspection apparatus includes: a stage part capable of traveling relative to optical systems with a substrate to be inspected mounted on the stage part; an illumination optical system for illuminating an inspection area on the substrate; a detection optical system for detecting light coming from the inspection area on the substrate; an image sensor for converting, to a signal, an image which is formed on the image sensor by the detection optical system; a signal processor for detecting defects by processing the signal from the image sensor; and a plane reflecting mirror, arranged between the detection optical system and the substrate, for transmitting the light, which comes from the substrate, to the detection optical system.

11 Claims, 16 Drawing Sheets

DEFECT INSPECTION METHOD AND DEFECT INSPECTION APPARATUS

CLAIM OF PRIORITY

This application is a continuation of U.S. application Ser. No. 12/038,274, filed Feb. 27, 2008 and claims priority from Japanese applications JP 2007-48355 filed on Feb. 28, 2007 and JP 2007-302997 filed on Nov. 22, 2007, the contents of which are hereby incorporated by reference into this application.

BACKGROUND OF INVENTION

1. Field of the Invention

The present invention relates to a defect inspection method and a defect inspection apparatus. Particularly, the present invention relates to a technology suitable for inspecting defects such as contaminating of foreign matters occurring in manufacturing processes, such as a semiconductor device manufacturing process, a liquid crystal display device manufacturing process and a printed circuit board manufacturing process, for manufacturing a product by forming a pattern on a substrate while detecting and analyzing the defects to take a countermeasure against the defects.

2. Description of the Related Art

In a semiconductor device manufacturing process, if there are foreign matters on a substrate (a wafer), the foreign matters pose a cause of defects such as defective electrical insulation and short circuits between interconnections. With the advancement of miniaturization of semiconductor devices, even finer foreign matters on a semiconductor device pose a cause of defective electrical insulation of its capacitor, or a cause of destruction of a gate oxide film and the like. Foreign matters are various. Some come from moving parts in the conveying equipment and the bodies of workers, and some are produced through chemical reaction of process gases in processing apparatuses. Others are contaminants in chemicals and materials used for manufacturing semiconductor devices.

A similar problem takes place in the liquid crystal display device manufacturing process. If foreign matters adhere onto, or some defect takes place in, a pattern formed on a liquid crystal display device substrate, the display device on the substrate becomes unusable any more. This is also the case with the printed circuit board manufacturing process. Adherence of foreign matters to the pattern poses a cause of short circuits and defective electrical connections in the pattern.

In the field of technology for detecting such foreign matters on a substrate to be inspected, Japanese Unexamined Patent Application Publication No. Sho. 62-89336 discloses the following technique. This patent document describes its technique as enabling highly reliable and sensitive inspection of foreign matters and defects while avoiding a false reporting that might be caused by a pattern. More specifically, foreign matters and defects are detected by irradiating the substrate with a laser beam, by detecting light scattering from foreign matters if the foreign matters adhere onto the substrate, and accordingly by comparing the result of the current detection with the result of the immediately preceding detection for another substrate of the same type. As well, Japanese Unexamined Patent Application Publication No. Sho. 63-135848 discloses a technique of irradiating a substrate with a laser beam, thus by detecting light scattering from foreign matters if the foreign matters adhere onto the substrate, and accordingly by analyzing the foreign matters thus detected by use of a technique of analyzing laser photoluminescence, a technique of analyzing two-dimensional X-ray magnetic resonance (XMR), or the like.

In another disclosed technique for inspecting foreign matters, a wafer is irradiated with coherent light, a spatial pattern removes light reflected from a repeated pattern on the wafer, and thereby foreign matters and defects, which do not appear repeatedly, are showed up and thus detected. In addition, Japanese Unexamined Patent Application Publication No. Hei. 1-117024 discloses a foreign matter inspecting apparatus designed to irradiate a circuit pattern formed on a wafer with light in a direction tilted at an angle of 45° to a main group of straight lines in the circuit pattern, and thereby preventing zeroth-order diffracted light, which comes from the main group of straight lines, from entering an aperture of its detection lens. This patent document also discloses that light from groups of straight lines, other than the main group of straight lines, are blocked by use of a spatial filter. As for an existing technique concerning an apparatus and a method for inspecting defects such as foreign matters, Japanese Patent Application Publication No. 2000-105203 discloses that a detection pixel is changed in size by switching detection optical systems. A technique for measuring the sizes of foreign matters is disclosed in each of Japanese Patent Application Publications Nos. 2001-60607 and 2001-264264. In a technique for detecting defects on a thin film, disclosed in Japanese Patent Application Publication No. 2004-177284, a beam spot oblong in a direction perpendicular to a direction in which the stage travels is formed on the thin film by focusing a laser light beam on the thin film, and the defects are detected in a direction perpendicular to the lighting direction.

SUMMARY OF THE INVENTION

For the purpose of detecting finer defects, the signal strength obtained from defects needs to be increased. The signal strength can be increased by enlarging a range in which a detection optical system receives light scattering from defects. To this end, it is effective that the detection optical system, arranged above the substrate to be inspected, is set to have a larger NA (numerical aperture). However, if the lens diameter is not enlarged, the distance between the apex of the lens and a substrate to be inspected needs to be narrowed. As a result, an angle at which the substrate is obliquely irradiated from out of the optical axis of the detection optical system cannot be increased. This lowers the power of light irradiated on the defects, and accordingly makes it impossible to strengthen the detection signal. On the other hand, when the lens diameter is enlarged, the distance between the apex of the lens and the substrate can be increased. If, however, the NA ratio is large, the ratio of the lens diameter to the focal length is accordingly larger. As a result, the optical system needs to be constructed in a considerably large size. This brings about a new problem of making it difficult to produce the lens, and to mount the lens on the apparatus.

There are some methods used for the purpose of causing a detection optical system to receive light reflecting from defects and scattering beyond a range where the detection optical system with a vertical optical axis is designed to receive light. One of the methods is to equip the detection optical system with a mechanism for tilting the optical axis of the detection optical system, and to detect defects by tilting the optical axis thereof. Another method is to additionally equip the detection optical system with an oblique optical system. However, the detection lens arranged above the substrate or the lens of the additionally-equipped oblique detection system comes into contact with the surface of the substrate to be inspected, when the angle of elevation from the defects is smaller than a certain angle. Thus, the detection optical system is not able to detect the defects when the angle of elevation from the defects is set too small. If the NA of the detection optical system and the diameter of the lens barrel are decreased for the purpose of preventing the optical axis from coming into contact with the surface of the substrate while lowering the angle of elevation from the defects, the detection optical system can somehow detect defects even at a small angle of elevation. However, in this case, the amount of light entering the detection optical system decreases, and accordingly the signal strength decreases. Moreover, the foregoing method requires the mechanism for tilting the optical system arranged above the substrate, or requires an image sensor, a lens, a spatial filter unit, and a detection area observing optical system, for the oblique detection. Accordingly, the method brings about problems that the optical system needs to be constructed in a larger size, that costs for parts increase, and that the number of steps for adjustment is added, for example.

An object of the present invention is to provide a defect inspection apparatus capable of detecting defects with a large range for receiving light scattering from fine defects while securing a sufficiently large signal strength, as well as a defect inspection method for the same.

A first aspect of the present invention is a method for optically inspecting a substrate to be inspected, which includes the steps of: illuminating the substrate; forming an image on a basis of light acquired from an illuminated area; and converting the image thus formed to a signal strength. The method is characterized in that light is transmitted through an optical element between the substrate and the image.

Another aspect of the present invention is an inspection apparatus characterized by including: a stage capable of traveling relative to an optical system with a substrate to be inspected mounted on the stage; an illumination system for illuminating an inspection area on the substrate; a detection optical system capable of allowing light from the substrate to enter the detection optical system, and thus capable of forming an image on an image sensor on a basis of light from the inspected area on the substrate; the image sensor for converting, to a signal, the image formed by the detection optical system; a signal processing system capable of detecting defects on a basis of the signal from the image sensor; and an optical element arranged between the detection optical system and the substrate. The inspection apparatus is also characterized in that the light from the substrate is capable of being transmitted to the detection optical system through the optical element.

Yet another aspect of the present invention is capable of inspecting defects obliquely by arranging a plane reflecting mirror between the detection lens and the substrate, thus reflecting the light acquired from the illuminated area by use of the plane reflecting mirror, and accordingly forming an image on an image sensor on a basis of the light thus reflected.

The present invention makes it possible to easily inspect defects obliquely at a smaller angle of elevation from the defects and with a larger NA, as well as to increase the number of types of detectable defects and the number of detectable defects.

DESCRIPTION OF THE PREFERRED EMBODIMENTS

Figure 1:
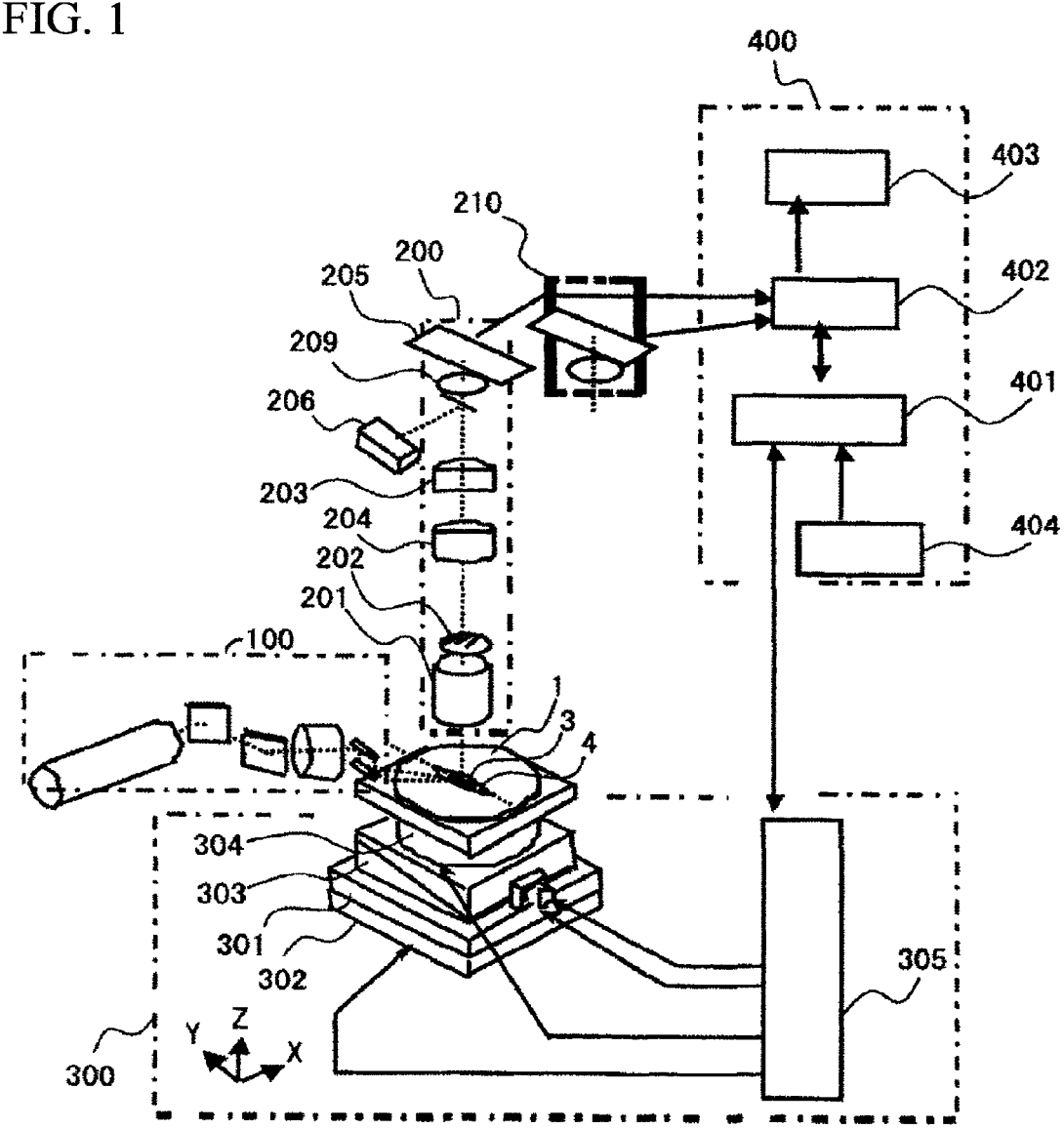
FIG. 1 is a diagram showing an example of a configuration of a defection inspection apparatus according to the present invention.

Descriptions will be provided hereinbelow for the embodiments of the present invention with reference to the drawings. The descriptions will be provided with components having the same function being denoted by the same reference numeral or symbol throughout the drawings.

Descriptions will be provided for a defect inspection apparatus according to an embodiment of the present invention with reference to FIG. 1.

The illustrated defect inspection apparatus includes a stage part 300, an illumination optical system 100, a detection optical system 200 and a control system 400. On the stage part 300, a substrate 1 to be inspected is mounted. With a light beam, the illumination optical system 100 illuminates a slit-shaped beam spot 3, which is a slit-shaped irradiation area, on the substrate 1 to be inspected. The detection optical system 200 detects light scattering from a detection area 4 in an image sensor. The control system 400 performs various arithmetic processes.

The stage part 300 includes an X stage 301, a Y stage 302 a Z stage 303, a θ stage 304, and a stage controller 305. The X stage 301 and the Y stage 302 scan an inspection area respectively in the X and Y directions in the substrate 1, and are movable relative to the optical systems. The Z stage 303 is capable of focusing on the surface of the substrate 1.

The illumination optical system 100 includes: a laser light source; a beam expander; an optical branching element (or mirror) being switchable among an optical filter group, a mirror and a glass plate; and a beam spot image forming part. It is desirable that the THG (third harmonic generation) of a high-power YAG laser with a wavelength of 350 nm should be used as the laser light source of the illumination optical system 100. However, the wavelength does not have to be 355 nm. An Ar laser, a nitrogen laser, a He—Cd laser, an excimer laser or the like may be used as the laser light source.

The detection optical system 200 is used for inspection from above. The detection optical system 200 includes a detection lens 201, a spatial filter 202, an image forming lens 203, a zoom lens group 204, a one-dimensional image sensor (an image sensor) 205, an observation optical system (a camera) 206 enabling the detection area in the image sensor to be observed, a reflected-beam splitter 209, and a branched-detection optical system 210 for performing simultaneous detections by use of two sensors. A CCD (Charge-Coupled Device) sensor or a TDI (Time Delay and Integration) sensor may be used for the one-dimensional image sensor 205. The CCD sensor may be considered to be suitable for linear detection, because each pixel is usually approximately 10 μm in size. The sensitivity of the CCD sensor does not decrease when an image out of focus in the scanning direction is acquired. In the case of the TDI sensor, on the other hand, it is desirable that the amount by which an image out of focus is acquired should be reduced by doing things such as narrowing the illumination width and tilting the TDI sensor, because the TDI sensor integrates images each corresponding to a specific number of pixels in the scanning direction. The coordinate system is shown in the lower left corner in FIG. 1. The X- and Y-axes are defined in the plane, and the Z-axis is defined so that the Z-axis extends upward perpendicularly to the plane. The optical axis of the detection optical system 200 is arranged along the Z-axis.

The control system 400 includes a signal processor 402, a control CPU part 401, a display part 403 and an input part 404. The signal processor 402 includes: an A/D (Analog-to-Digital) converter; a data memory capable of delaying a signal; a differential processing circuit for computing the difference between signals in each of the chips; a memory in which the difference between signals in each of the chips is stored temporarily; a threshold value calculating processor for setting up a pattern threshold value; and a comparator. The control CPU part 401 stores a result of detecting defects including foreign matters, and concurrently controls output means for outputting the result of detecting defects, as well as drives of the motors, the coordinate, and the sensor.

Figure 2A:
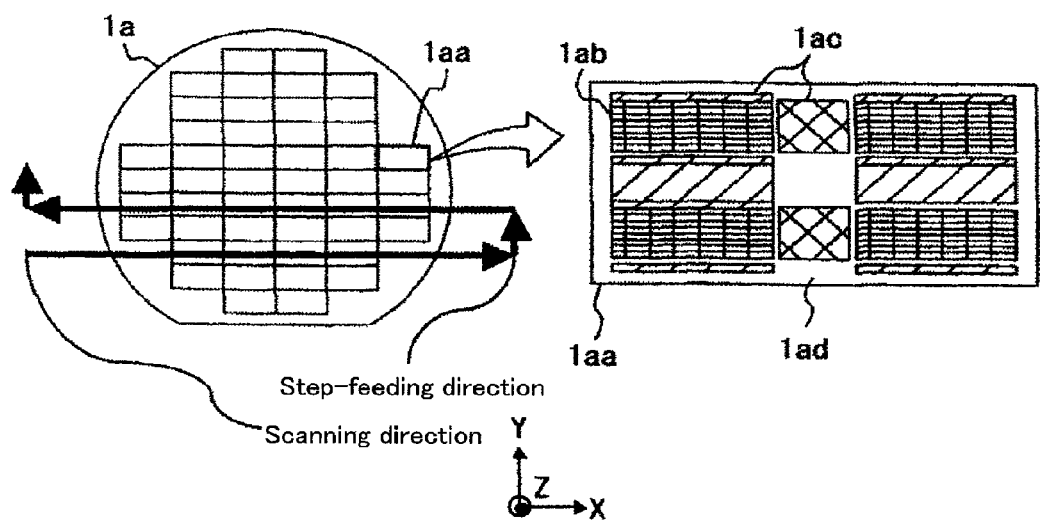
FIGS. 2A and 2B are diagrams showing a substrate to be inspected on which large-scale integrated circuits (LSI) as inspection objects are arrayed.

Descriptions will be provided for a workpiece which is inspected by the defect inspection apparatus according to the present invention. A substrate 1a to be inspected shown in FIG. 2A includes memory LSI chips 1aa which are arrayed at predetermined intervals two-dimensionally. Each memory LSI chips 1aa chiefly includes: a memory cell area 1ab; peripheral circuit areas 1ac each including a decoder, a control circuit or the like; and the other area 1ad. The memory cell area 1ab has a cell pattern in which cells are arrayed two-dimensionally regularly, or a repetitive cell pattern. The peripheral areas 1ac have a cell pattern in which cells are arranged two-dimensionally irregularly, or an unrepetitive cell pattern.

Figure 2B:
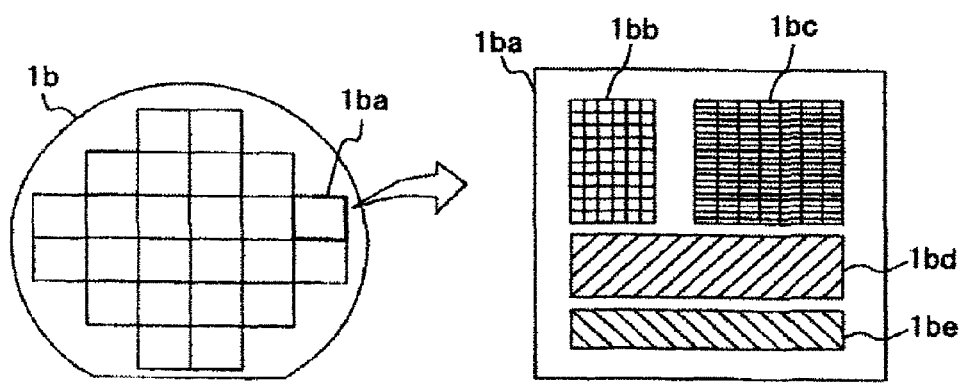

A substrate 1b to be inspected shown in FIG. 2B includes LSI chips 1ba used for microcomputers and the like, which are arrayed at predetermined intervals two-dimensionally. Each LSI chip 1ba for microcomputers and the like chiefly includes a register group area 1bb, a memory part area 1bc, a CPU core part area 1bd, and an input-output part area 1be. Incidentally, FIG. 2B schematically shows how the memory part area 1bc, a CPU core part area 1bd, and an input-output part area 1be are arrayed. Each of the register group area 1bb and the memory part area 1bc has a pattern in which cells are arrayed two-dimensionally regularly, or a repetitive pattern. Each of the CPU core part area 1bd and the input-output part area 1be has an unrepetitive pattern. As described above, an object which is inspected by the defect inspection apparatus according to the present invention generally has chips which are regularly arrayed like any one of the substrates (wafers) shown in FIGS. 2A and 2B. However, in each chip, minimum line widths are different from one area to another. Each chip has repetitive patterns and unrepetitive patterns. The configurations of the respective chips are various.

Figure 3:
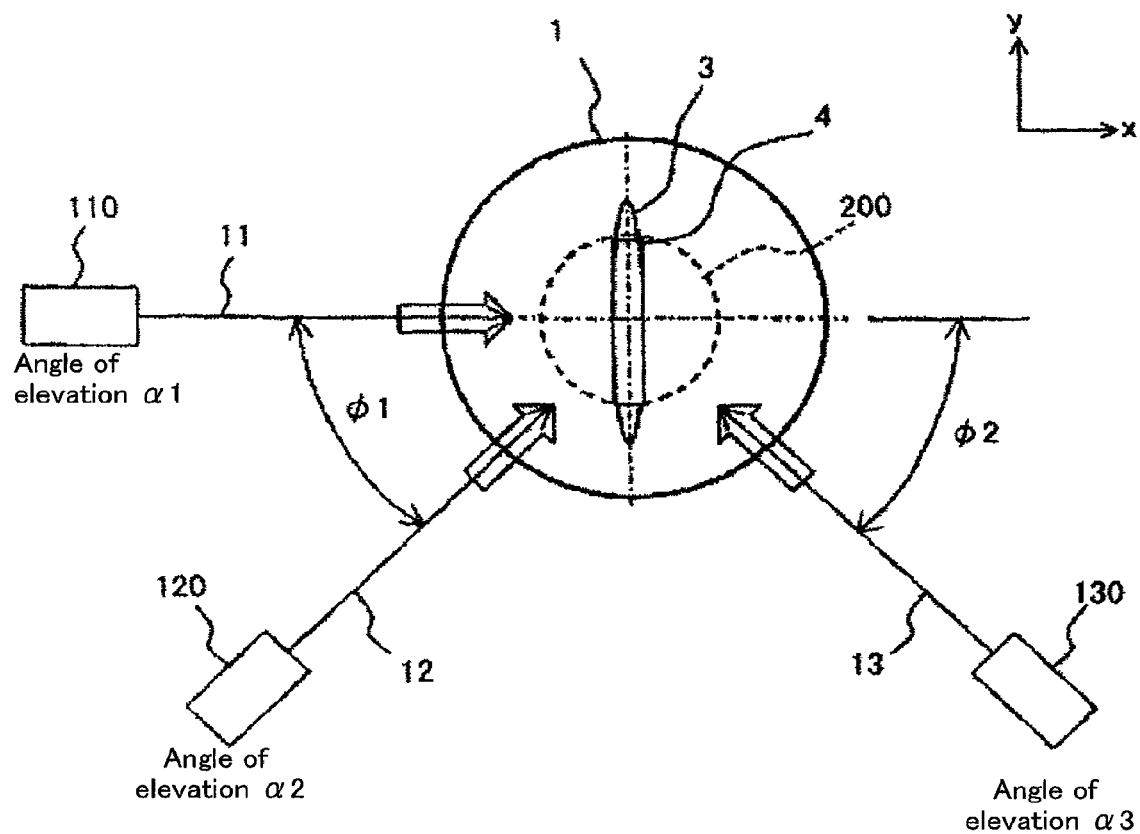
FIG. 3 is a diagram illustrating three illumination light beams used for inspection, which are generated by an illumination optical system in the defect inspection apparatus according to the present invention.

Descriptions will be provided for a first to third beam spot image forming part 110, 120 and 130 with reference to FIG. 3. FIG. 3 shows how the substrate 1 looks when viewed from above.

An illumination light beam 11 for inspection in the X-axis direction is irradiated on the surface of the substrate 1 through the first beam spot image forming part 110. An illumination light beam 12 for inspection in a direction at an angle of −45° to the Y-axis direction is irradiated on the surface of the substrate 1 through the second beam spot image forming part 120. An illumination light beam 13 for inspection in a direction at an angle of 45° to the Y-axis direction is irradiated on the surface of the substrate 1 through the third beam spot image forming part 130.

These illumination light beams 11, 12 and 13 are irradiated on the surface of the substrate 1 at a predetermined elevation angle a for the surface thereof. Particularly when the elevation angle a at which the illumination light beams 12 and 13 are irradiated on the surface is reduced, it is possible to decrease the amount detected light scattering from the bottom surface of the transparent thin film. These illumination light beams 11, 12 and 13 forms the beam spot 3, which is oblong, on the substrate 1. The length of the beam spot 3 in the Y-axis direction is longer than the length of a detection area 4 of the image sensor as the one-dimensional image sensor 205 in the detection optical system 200.

Descriptions will be provided for why the illumination optical system 100 is provided with the three beam spot image forming parts 110,120 and 130. An angle between an image formed when the illumination light beam 12 is projected on the XY-plane and the X axis is denoted by $\phi 1$, whereas an angle between an image formed when the illumination light beam 13 is projected on the XY-plane and the X axis is denoted by $\phi 2$. In the case of the present example, $\phi 1 = \phi 2 = 45°$. In this case, since an unrepetitive pattern on the substrate 1 is a linear pattern which extends chiefly in the X-axis direction or the Y-axis direction, the illumination light beams 12 and 13 are irradiated on the pattern at an angle of 45° to the pattern. As its X-axis component and Y-axis component, the diffracted light enters the incident pupil of the detection lens 201. However, in a case where the elevation angle $\alpha$ at which the illumination light beams 12 and 13 are irradiated on the pattern is small, specular reflection light reflects off the pattern at a small angle equal to α. As a result, the X-axis component and the Y-axis component of the diffracted light similarly come away from the incident pupil of the detection lens 201. For this reason, it is possible to prevent the diffracted light from entering the detection optical system 200. Since this point is described in detail, for example, in Japanese Patent No. 3566589 (see particularly paragraphs [0033] to [0036]), the description thereof will be omitted here.

Unrepetitive patterns on the substrate 1 are chiefly linear patterns formed in parallel to, and perpendicular to, one another. These linear patterns extend in the X-axis direction and the Y-axis direction. Since the patterns on the substrate 1 are formed in a protruding manner, a concave portion is formed between each two adjacent linear patterns. Accordingly, the illumination light beams 12 and 13 irradiated on the surface of the substrate 1 at angles of 45° to the X axis and the Y-axis are blocked by protruding circuit patterns. As a result, concave portions between the adjacent linear patterns cannot be irradiated.

With this taken into consideration, the first beam spot image forming part 110 for generating the illumination light beam 11 in the X-axis direction is provided to the illumination optical system 100. The illumination light beam 11 for the inspection is thus capable of being irradiated on concave portions between linear patterns. Accordingly, defects existing there, inclusive of foreign matters, are capable of being detected. Depending on the direction in which the linear pattern extends, the workpiece may be inspected after turning the workpiece at an angle of 90°. Otherwise, the illumination light beam 11 may be irradiated on the surface of the substrate in the Y-axis direction.

It should be noted that, in the case where concave portions between linear patterns are irradiated in the X-axis direction with the illumination light beam 11 zeroth-order diffracted light needs to be blocked in order that the image sensor should not detect the zeroth-order diffracted light. To this end, the spatial filter 202 is provided.

Figure 4A:
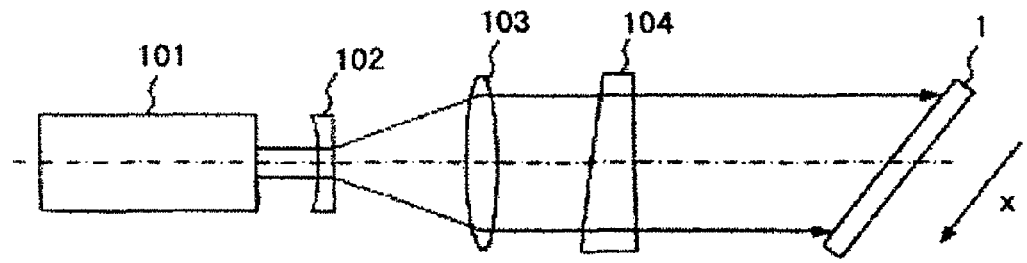
FIGS. 4A and 4B are diagrams showing an optical system including an illumination lens in the illumination optical system in the defect inspection apparatus according to the present invention.
Figure 4B:
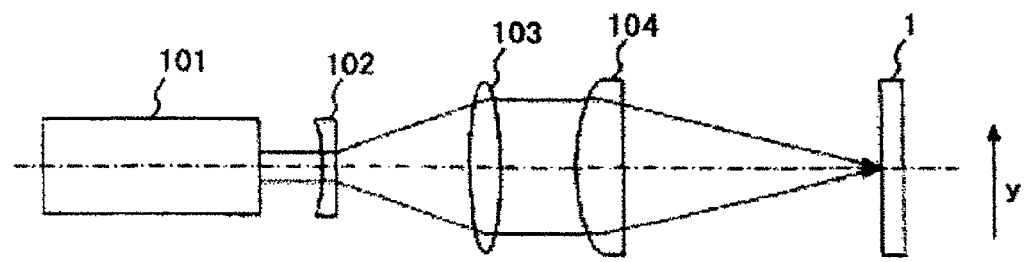
Figure 5:
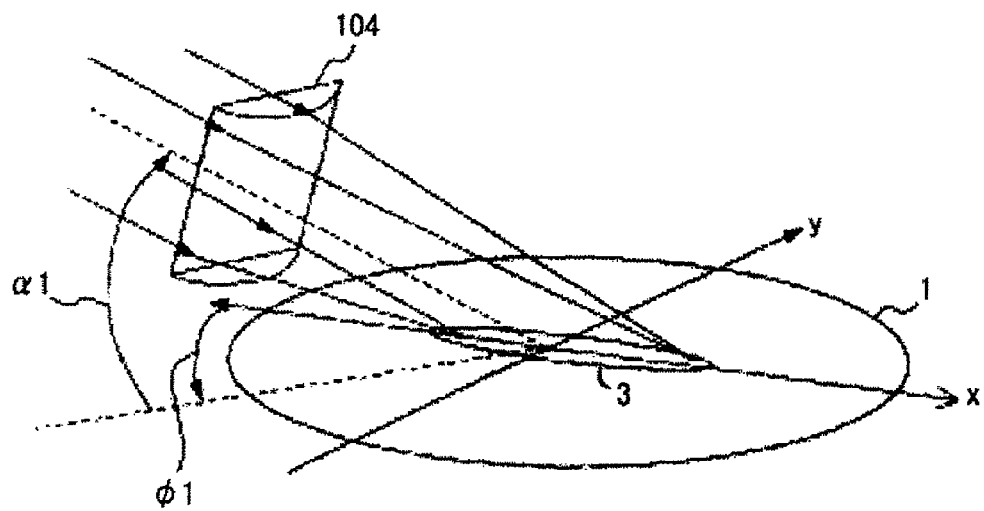
FIG. 5 is a diagram illustrating a function of the illumination lens in the illumination optical system in the defect inspection apparatus according to the present invention.

Descriptions will be provided for how the oblong beam spot 3 is formed with reference to FIGS. 4 and 5. FIGS. 4 and 5 show only a laser light source 101, a concave lens 102, a convex lens 103 and an illumination lens 104 in the illumination optical system 100, and the other components therein are omitted.

The illumination lens 104 is a cylindrical lens having a conical curved surface. As shown in FIG. 4A, the focal length of the illumination lens 104 linearly changes in the longitudinal direction (in the vertical direction in FIG. 4A). As shown in FIG. 4B, the illumination lens 104 has a cross-section as a planoconvex lens. As shown in FIG. 5, the illumination lens 104 is capable of generating the slit-shaped beam spot 3 by constricting the illumination light, which obliquely enters the substrate 1, in the Y-axis direction, and by collimating the resultant illumination light in the X-axis direction. α1 denotes the angle (the elevation angle) of the illumination light to the surface of the substrate 1, and φ1 denotes the angle formed by the X-axis and an image of the illumination light 11, which is projected on the substrate 1.

Use of such an illumination lens 104 makes it possible to generate the illumination which has light rays parallel to one another in the X-axis direction, and which is at φ1 nearly equal to 45°. The illumination lens 104 having the conical curved surface can be manufactured by use of the publicly-known technology. The manufacturing method and the like are described in detail, for example, in Japanese Patent No. 3566589 (see paragraphs [0027] to [0028] in particular).

[First Embodiment]

Figure 6:
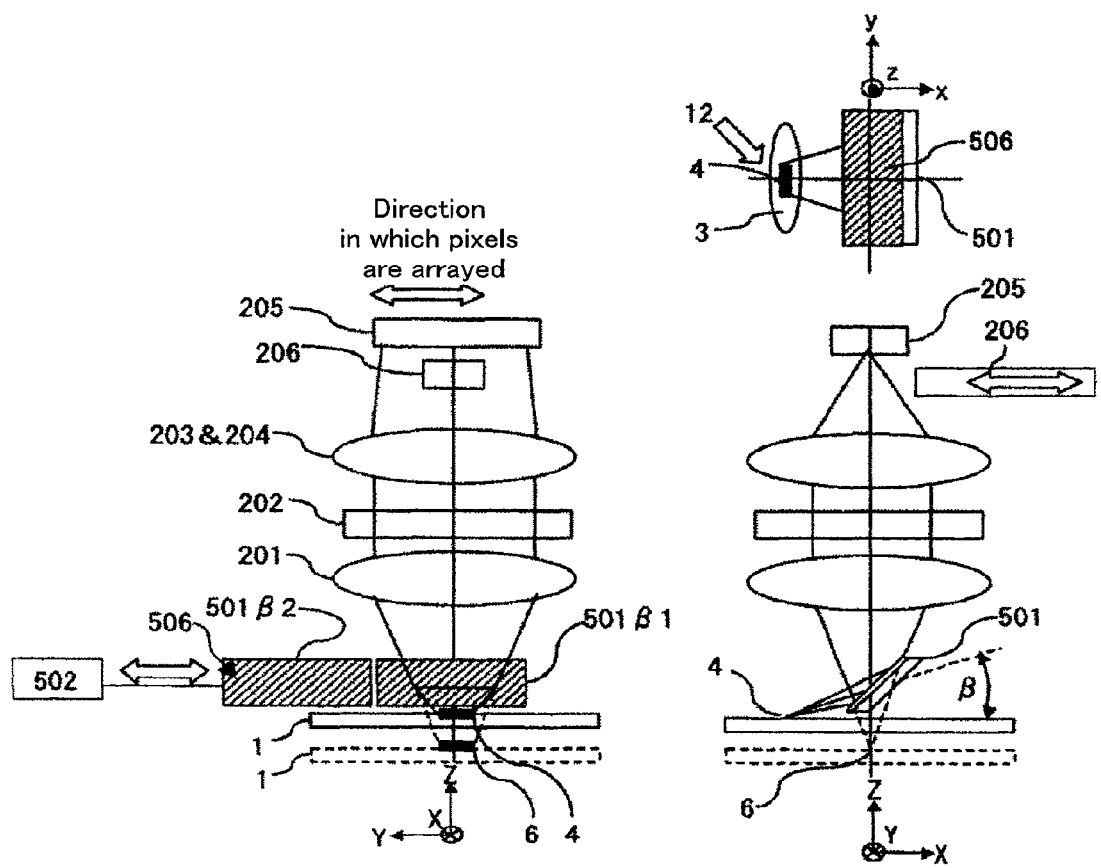
FIG. 6 is a diagram illustrating a first embodiment of the present invention.

Descriptions will be provided for a first embodiment of an oblique inspection according to the present invention by use of FIG. 6. An object of the present embodiment is to accomplish a method characterized by enabling the oblique inspection by use of the detection optical system for inspection from above in order that defects on the substrate 1 can be detected optically.

A plane reflecting mirror 501 is arranged between the detection lens 201 and the substrate 1. This plane reflecting mirror 501 reflects the obliquely scattering light, which is obtained from the detection area 4 of the image sensor located above the substrate 1. The scattering light reflected by the plane reflecting mirror 501 forms an image on the image sensor 205 through the detection optical system. To this end, the reflecting surface of the plane reflecting mirror 501 is arranged in parallel to a direction in which the pixels are arrayed in the image sensor (in the longitudinal direction) and concurrently tilted to the optical axis of the detection lens. The detection area 4 does not have to meet the optical axis of the detection lens. The detection area 4 can be set up in a location shifted in a direction perpendicular to the direction in which the pixels are arrayed in the image sensor 205, or in the X-axis direction. Thereby, the oblique inspection is capable of being carried out.

For the purpose of avoiding the eclipse of the light path, the shape of the plane reflecting mirror 501 in the Y-axis direction needs to be sufficiently larger than the diameter of the light path corresponding to the NA of the detection lens 201. After the elevation angle β for the oblique detection is determined, it is desirable that the length of the reflecting surface should be at maximum under a condition that the length of the reflecting surface does not allow the plane reflecting mirror 501 to contact the detection lens 201 or the substrate 1 when a switch is made between the detection lens 201 and the substrate 1. A clearance of 0.2 mm to 1 mm, for example, is secured between the detection lens 201 and the substrate 1. In this case, when the bottom surface and the top surface of the plane reflecting mirror 501 are positioned to be horizontal, a maximum reflecting area can be secured. It is desirable that the plane reflecting mirror 501 should be positioned in the X-axis direction at a location capable of maximizing the NA of the light entering the plane reflecting mirror 501.

When the light from the detection area 4 of the image sensor 205 is going to be formed into an image on the image sensor 205, the detection lens 201 needs to be focused on the detection area 4 in the image sensor. To this end, it is desired that, in this case, the detection lens 201 should be focused on the detection area 4 for the oblique inspection by use of an auto-focus mechanism after raising the Z stage 303 up to a height which causes the detection lens 201 to focus on the detection area 6 for the inspection from above. In a case where the optical axis of the auto-focus mechanism passes the inside of the detection lens, the position of the auto-focus mechanism need not be changed when the oblique inspection is going to be carried out. However, in a case where an off-axis auto-focus mechanism whose optical axis does not pass the inside of the detection lens is used, the auto-focus mechanism needs to be moved by a distance +ΔZ in the Z-direction in response to the movement ΔZ of the Z-stage. Otherwise, a method can be also used, in which the X-, Y- and Z-coordinates of the substrate 1 are beforehand stored, and the distribution of the surface heights are found. In the method, the distribution is then reproduced when the inspection is carried out. In addition, when the light from the detection area 4 of the image sensor 205 is going to be formed into the image on the image sensor 205, it is desired that the center and angle of the distribution of the beam spot 3 should be made to agree with the detection area 4 of the image sensor.

The plane reflecting mirror 501 includes a mechanism capable of sending the plane reflecting mirror 501 in and out of the light path by use of a switching mechanism 502. In the case of the present invention, when the inspection is carried out by causing the light from the detection area 6 of the image sensor for the inspection from above to be formed into an image on the image sensor 205 by use of the detection optical system 200 (when the inspection is carried out from above), the plane reflecting mirror 501 is withdrawn out of the light path. When the inspection is carried out by causing the light from the detection area 4 of the image sensor to be formed into an image on the image sensor 205 by use of the detection optical system 200 (when the inspection is carried out by the oblique inspection), the plane reflecting mirror 501 is returned to a position shown in FIG. 6.

Thereby, the detection optical system for the oblique inspection in which the plane reflecting mirror 501 is put in the light path as well as the detection optical system for the inspection from above in which the plane reflecting mirror 501 is put out of the light path are formed. This makes it possible to choose between the oblique inspection and the inspection from above. A result of the inspection from above and a result of the oblique inspection can be obtained through carrying out the two inspections. This makes it possible to more precisely calculate the size of a defect located in the coordinates assigned for the inspection from above which are the same as the coordinates assigned for the oblique inspection, and to more precisely classify the defect, on the basis of the signal intensity and defective area acquired through each of the inspection from above and the oblique inspection.

It is desirable that the plane reflecting mirror 501 should have a mechanism capable of changing the elevation angle of light entering the plane reflecting mirror 501 in accordance with the distribution of light scattering from a defect which is intended to be detected. With this mechanism, the oblique inspections are performed at different angles of elevation, both the detected signal strengths and corresponding sets of coordinates are stored in a memory in the signal processing system, and then the signal strengths obtained by the oblique inspection at the different angles of elevation are compared with each other. As a result, extraction and classification of defects can be carried out with higher accuracy. In FIG. 6, the angle of elevation used for scattering light to be detected is switched between $\beta 1$ and $\beta 2$ by moving two plane reflecting mirrors 501 in a direction indicated by the illustrated left-right white arrow by use of the switching mechanism 502. The two plane reflecting mirrors 501 cause the scattering light as the result of the angles $\beta 1$ and $\beta 2$ of elevation, respectively, to enter the detection lens 201. Accordingly, the oblique inspection for the scattering light at different angles of elevation for the detection can be carried out by switching the angle of elevation between the plane reflecting mirrors 501. It is desirable that the angle $\beta$ of elevation for the detection should be set at a value which enables the rest of NA, which is uncovered by the intrinsic NA of the detection lens 201 located above, to be covered by NAs respectively brought about by $\beta 1$ and $\beta 2$. The setting of $\beta$ in such a manner makes it possible to detect the light scattering from the defect with NA larger than 0.9 in the X-axis direction, and thus to increase the signal strength representing the defect which causes an oriented distribution of the scattering light, as well as accordingly to increase the sensitivity. With the method described above, according to the present embodiment, a range in which the defect inspection apparatus receives light scattering from fine defects can be enlarged, and concurrently, the signal strengths can be increased.

The detection area 6 of the image sensor is inspected from above while changing the magnification of its inspection image by changing the position of the zoom lens group 204. Likewise, the oblique inspection method of the present embodiment makes it possible to obliquely inspect the detection area 4 of the image sensor while changing the magnification of its inspection image by changing the position of the zoom lens group 204. This makes it possible to change the size of pixels for detecting the defect on the substrate 1. As a result, in a case where the pixel size is set smaller, it is possible to increase S/N (which represents the signal strength of the defect divided by the signal strength of the pattern). In a case where the pixel size is set larger, a time required to obtain a certain throughput can be reduced.

An image obtained by applying the Fourier transform to the detection area 6 of the image sensor can be filtered by use of the spatial filter 202 while the inspection from above is being carried out. Likewise, in the oblique inspection method of the present embodiment, an image obtained by applying the Fourier transform to the detection area 4 of the image sensor can be filtered by use of the spatial filter 202. That is because the image obtained as the result of the application of the Fourier transform in the direction in which the pixels are arrayed depends on the pattern pitch.

The detection area 6 of the image sensor is capable of being observed by use of the observation optical system 206 while the inspection from above is being carried out. Likewise, in the oblique inspection method of the present embodiment, the detection area 4 of the image sensor is capable of being observed by use of the observation optical system 206 as the detection optical system. Accordingly, an additional observation function for the oblique inspection is unnecessary to be provided to the defect inspection apparatus.

[Second Embodiment]

Figure 7:
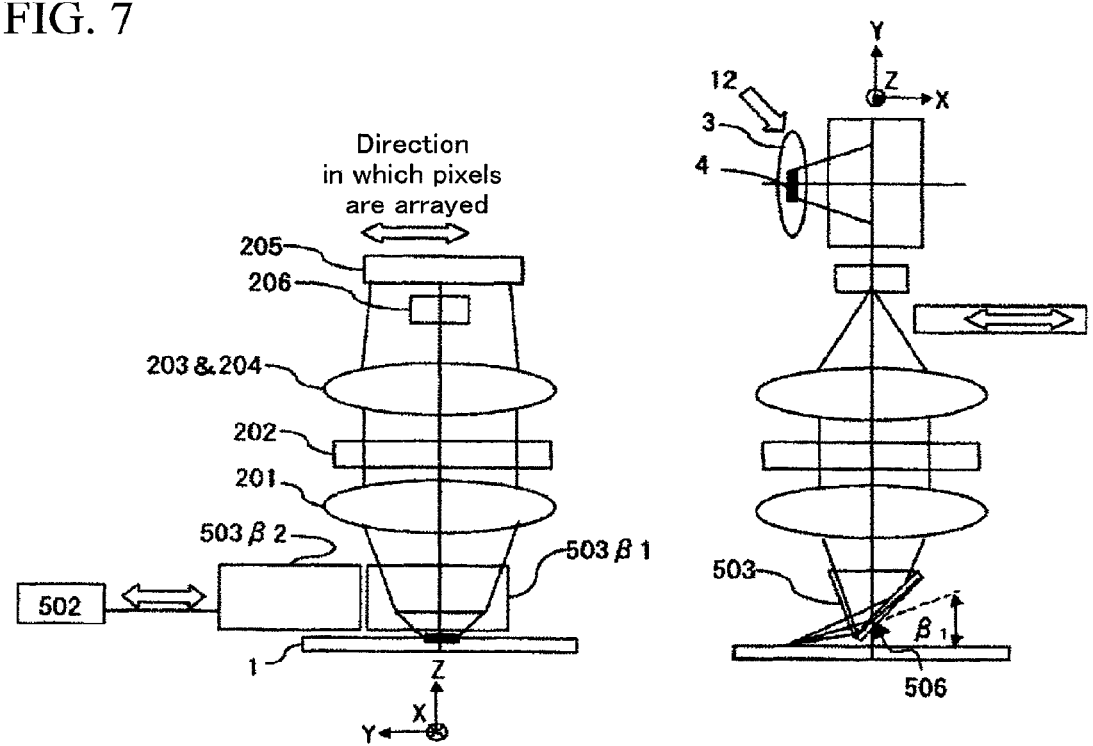
FIG. 7 is a conceptual diagram of a second embodiment of the present invention.

Descriptions will be provided for a second embodiment of the oblique inspection method according to the present invention by use of FIG. 7. An object of the present embodiment is to accomplish a method which, unlike the method according to the first embodiment, makes it possible to carry out the inspection from above and the oblique inspection without changing the heights of the respective stages, by making the height of the stage for the inspection from above using the detection optical system equal or approximate to the height of the stage for the oblique inspection using the same detection optical system, and thus by causing the height of correct focus of the auto-focus system to follow its retraction within a range of the retraction. To this end, it is desirable that the length of the light path from the inspection area on the substrate 1 to the detection lens 201 should be extended by arranging a light path length correcting element 503 between the plane reflecting mirror (a reflecting surface 506 of the light path length correcting element 503 in the case of the present example) and the detection optical system 200. The length of the light path can be extended by a distance equal to a value obtained by multiplying 1/(1−the refractive index of the correcting element 503) by the length of a part of the light path which passes the inside of the correcting element 503. The method according to the second embodiment is characterized in that use of a prism for the light path length correcting element 503 makes the amount of correction larger than a method according to a third embodiment. A dielectric multilayered coating for reflecting light rays entering the light path length correcting element 503 with a higher reflectance is formed on one surface (the reflecting surface 506) of the light path length correcting element 503. FIG. 7 shows that the oblique inspection method according to the present embodiment is configured to switch the angle of elevation used for scattering light to be detected between β1 and β2 by moving the two light path length correcting elements 503 in a direction indicated by a left-right white arrow of FIG. 7 by use of the switching mechanism 502. One light path length correcting element 503 assigning one of the two different angles to its reflecting surface 506 causes the scattering as the result of the angle β1 of elevation to enter the detection lens 201, and the other light path length correcting element 503 assigning the other of the two different angles to its reflecting surface 506 causes the scattering light as the result of the angle β2 of elevation to enter the detection lens 201 In addition, although the method according to the first embodiment obtains correct focus of the detection optical system by raising the Z stage 303 when its inspection mode is changed from the inspection from above to the oblique inspection, the method according to the second embodiment enables the inspection from above to be carried out with the stage positioned at the same height as the stage is positioned when the scattering light from the detection area 4 for the oblique inspection in the image sensor is detected, because the light path length correcting element 5 is arranged therein. This makes it unnecessary that the height of the stage should be corrected, or that a coarse adjustment mechanism should be provided.

It is desirable that the light path length correcting element 503 should include an image-forming aberration correcting function. The forming of a curve for correcting the aberration on the emission surface of the light path length correcting element 503 makes it possible to prevent the image forming performance from being deteriorated. Thereby, it is possible to correct the aberration of light passing the peripheral portion of the detection optical system having a high NA. As a result, it is possible to reduce the intensity distribution of an image whose light is received by the image sensor, and to decrease the sensitivity unevenness.

[Third Embodiment]

Figure 8:
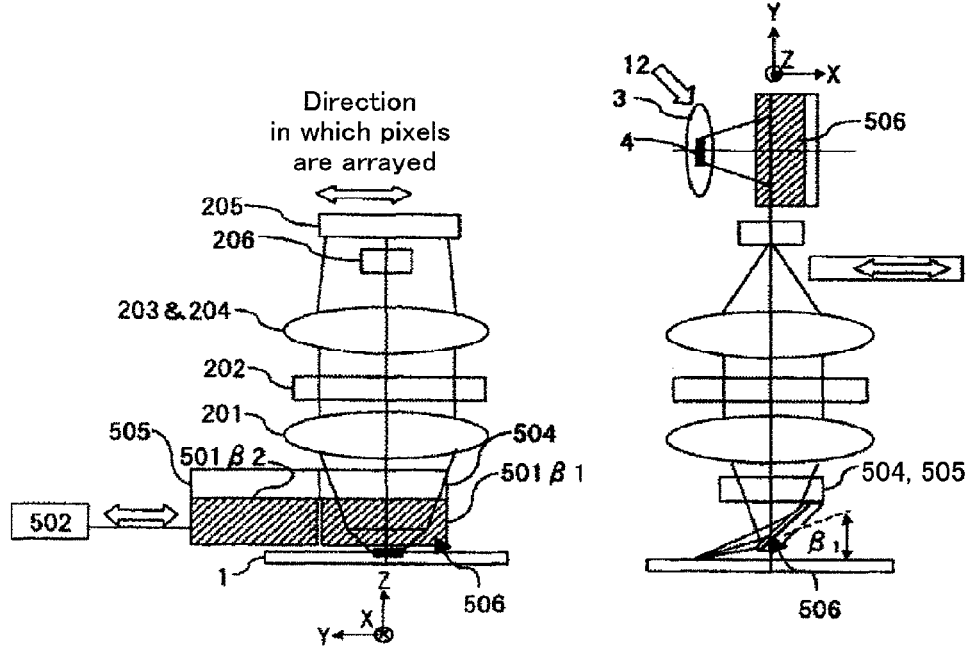
FIG. 8 is a conceptual diagram of a third embodiment of the present invention.
Figure 9:
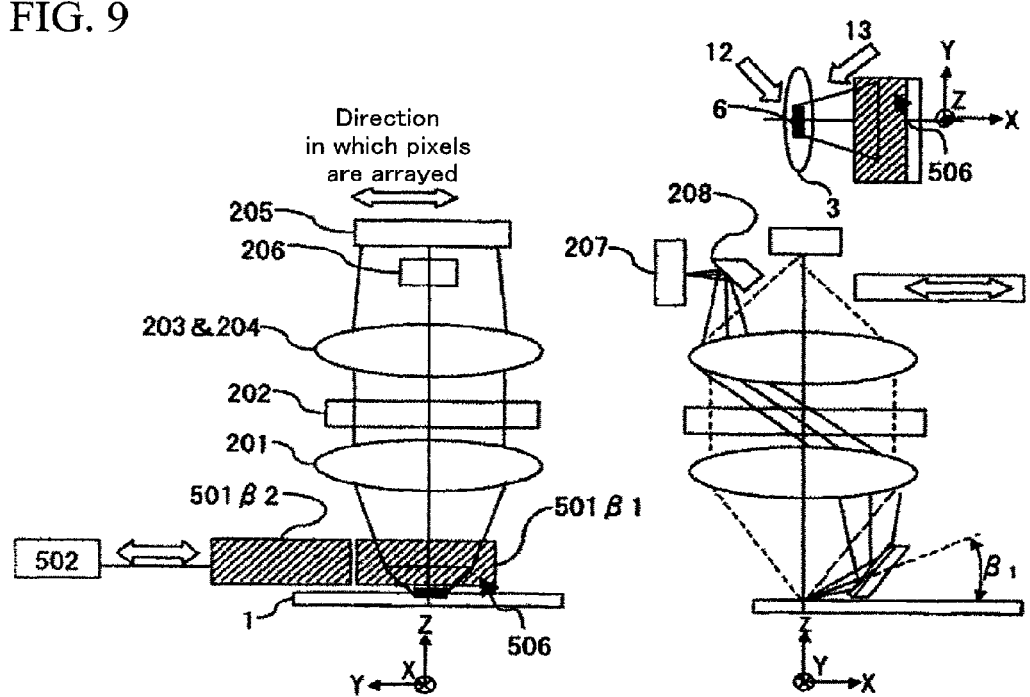
FIG. 9 is a conceptual diagram of a fourth embodiment of the present invention.
Figure 10:
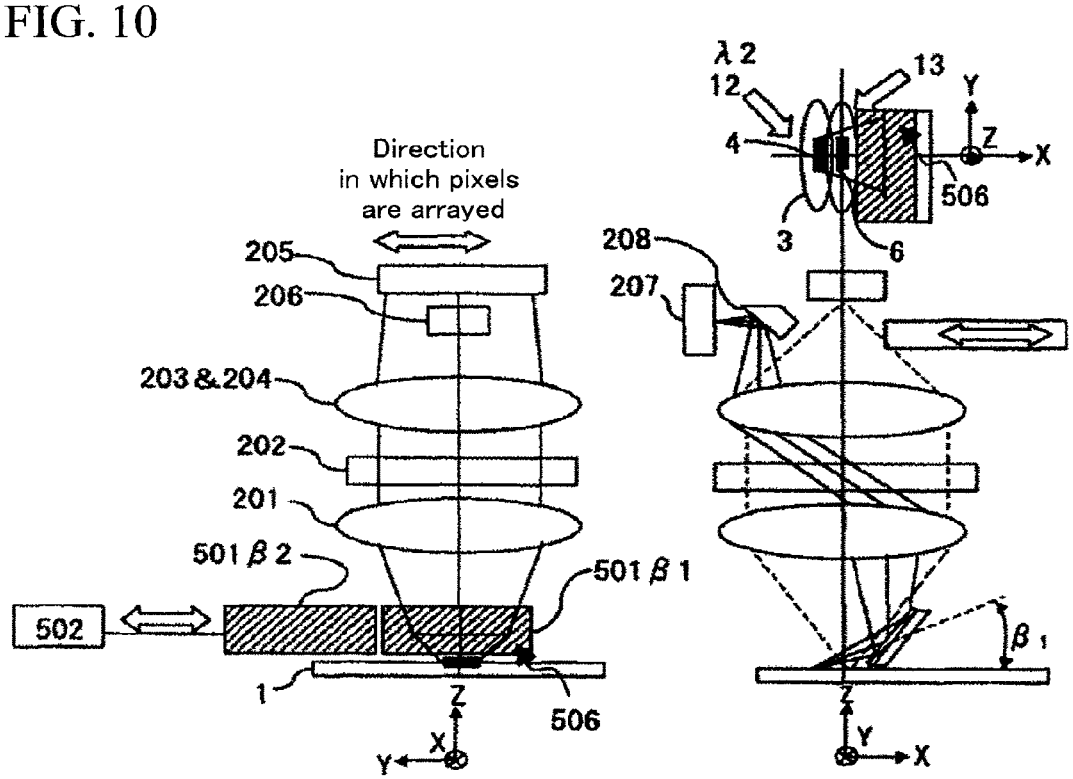
FIG. 10 is a conceptual diagram of a fifth embodiment of the present invention.

Descriptions will be provided for a third embodiment of the oblique inspection according to the present invention by use of FIG. 8. An object of the present embodiment is to accomplish a method which makes it possible to carry out the inspection from above and the oblique inspection without changing the heights of the respective stages, by making the height of the stage for the inspection from above using the detection optical system equal to the height of the stage for the oblique inspection using the same detection optical system, and thus by causing the height of correct focus of the autofocus system to follow its retraction within a range of the retraction. To this end, it is desirable that the length of the light path should be extended by arranging any one of a light path length correcting element 504 and a light path length correcting element 505 between a corresponding one of the two plane reflecting mirrors 501 and the detection optical system 200. It is possible to extend the length of the light path by a distance equal to a value obtained by multiplying 1/(1−the refractive index of the correcting element 504 or 505) by the length of a part of the light path which passes the inside of the correcting element 504 or 505. FIG. 8 shows that the oblique inspection method according to the present embodiment is configured to switch the angle of elevation used for scattering light to be detected between β1 and β2 by moving the two plane reflecting mirrors 501 in a direction indicated by a left-right white arrow of FIG. 8 by use of the switching mechanism 502. One plane reflecting mirror 501 causes the scattering light as the result of the angle β1 of elevation to enter the detection lens 201 at one of the two different angles, and the other plane reflecting surface 501 causes the scattering light as the result of the angle β2 of elevation to enter the detection lens 201 at the other of the two different angles. The light path length correcting element 504 and 505 are respectively provided on these two plane reflecting mirrors 501. It is necessary that the emission surface of each of the light path length correcting elements 504 and 505 should be aspheric so as to prevent the image forming performance from being deteriorated. Thereby, it is possible to correct the aberration of light passing the peripheral portion of the detection optical system having a high NA. As a result, it is possible to reduce the intensity distribution of an image whose light is received by the image sensor 205, and to decrease the sensitivity unevenness. Unlike the second embodiment, the present embodiment makes it easier to process the aspheric surfaces of the light path length correcting elements because the light path length correcting elements are shaped like a lens. On the other hand, the length of the light path is shorter in the present embodiment than in the second embodiment. As a result, when the angle β of elevation for the oblique detection system is smaller, the amount of correction becomes insufficient. To avoid this, it is desirable that a prism should be used for the light path length correcting elements 504 and 505 as in the case of the light path length correcting element 503 according to the second embodiment when the angle β of elevation is smaller.

[Fourth Embodiment]

Descriptions will be provided for a fourth embodiment of the oblique inspection according to the present invention. An object of the present embodiment is to accomplish a method which makes it possible to inspect defects on the basis of light from a single detection area (the detection area 6 in the case of the present example) by use of one or more image sensors for one inspection. In other words, this method makes it possible to detect the light from the detection area 6 by use of the image sensor 205 used for the inspection from above and an image sensor 207 which is additionally provided for the oblique inspection. To this end, it is desirable that the method should be that in which the plane reflecting mirrors 501 are positioned at their respective locations shifted from the optical axis of the detection optical system 200, and which causes light reflected by each of the plane reflecting mirrors 501 to enter the peripheral portion of the detection lens 201. A plane reflecting mirror 208 for branching a light path is arranged in the light path of the light reflected by each of the plane reflecting mirrors 501. Thus, light obliquely scattering from the detection area 6 of the image sensor is reflected by the plane reflecting mirror 208 for branching a light path, and is formed into an image on the image sensor 207 for the oblique inspection. At this time, the light path for the oblique inspection is different from the light path (indicated by broken lines) for the inspection from above. The inspection from above and the oblique inspection can be carried out simultaneously if the plane reflecting mirror 208 for branching a light path is placed out of the area for the inspection from above (or out of the light path for the inspection from above). At this time, a light path length correcting element may be added to the optical system for the oblique detection, as in the case of the optical system for the oblique detection according to the second and third embodiments.

An effect brought about by the simultaneous performance of the inspection from above and the oblique inspection is to shorten time needed to inspect defects. The method according to the present embodiment makes it possible to simultaneously receive two signals representing the angles of elevation for each of the inspections, and thus to carry out the inspections while doing arithmetic on the signals. As a result, the memory capacity of the hardware can be saved, and time and workload needed for the process using the software can be reduced. The present embodiment makes the wavelength and deflection different between the illumination light beam 12 and the illumination light beam 13, and thus makes it possible to obtain information on a signal strength from the image sensor 205, and information on the other signal strength from the image sensor 207, by a one-time inspection, where the two signal strengths are different from each other. The signal strength representing the light scattering from the defect is different depending on what wavelength, deflection, and angle of elevation from the inspection are selected for each illumination light beam. Accordingly, it is possible to more precisely extract information on defect classification when the ratio of the signal strength from the image sensor 205 and the signal strength from the image sensor 207 is used as a characteristic amount.

[Fifth Embodiment]

Descriptions will be provided for a fifth embodiment of the oblique inspection according to the present invention. An object of the present embodiment is to accomplish a method which makes possible to simultaneously carry out the inspection from above in which light from the detection area 6 is detected by the image sensor 205 and the oblique inspection in which light from the detection area 4 is detected by the image sensor 207. To this end, it is desirable that the method should be that in which the plane reflecting mirrors 501 are positioned out of the optical axis of the detection optical system 200, and which causes light reflected by each of the plane reflecting mirrors 501 to enter the peripheral portion of the detection lens 201. At this time, a light path length correcting element may be added to the optical system for the oblique inspection, as in the case of the optical system for the oblique inspection according to the second and third embodiments. The present invention is different from the fourth embodiment in that the detection area 4 of the image sensor for the oblique inspection is arranged at a location shifted from the detection area 6 of the image sensor for the inspection from above. In order to form an image representing the detection area 4 of the image sensor, on the image sensor 207 as the image sensor for the oblique inspection, the plane reflecting mirror 208 for branching a light path is arranged in the light path of the light reflected by each of the plate reflecting mirrors 501, and thus the light path of the light thus reflected is branched. At this time, the light path for the inspection from above is indicated by broken lines. The inspection from above and the oblique inspection can be carried out simultaneously if the plane reflecting mirror 208 for branching a light path is placed out of the area for the inspection from above (or out of the light path for the inspection from above).

An effect brought about by the simultaneous performance of the inspection from above and the oblique inspection is to shorten time needed to inspect defects. The method according to the present embodiment makes it possible to simultaneously receive two signals representing the angles of elevation for each of the inspections, and thus to carry out the inspections while doing arithmetic on the signals. As a result, the memory capacity of the hardware can be saved, and time and workload needed for the process using the software can be reduced. The present embodiment is different from the fourth embodiment in the following point. The location in which the light reflected by each of the plane reflecting mirrors 501 enters the detection lens 201 is closer to the optical axis of the detection optical system 200 in the present embodiment than in the fourth embodiment by shifting the position of the detection area 4 for the oblique inspection along with the position of the detection area 6 for the inspection from above. As a result, the present embodiment makes it possible to reduce the field of view of the detection optical system, and accordingly to reduce the deterioration of the image forming performance of the light passing the peripheral portion of the lens. In addition, the present embodiment makes it possible to select the direction, angle of elevation, deflection, and wavelength of the illumination as conditions for the illumination. Accordingly, the present embodiment enables a defect to be defected while causing an image representing the defect to be formed on the multiple image sensors. In addition, like the fourth embodiment, by making the direction, angle of elevation, wavelength, and deflection different between the illumination light beams 12 and 13, the present embodiment makes it possible to obtain information on a signal strength from the image sensor 205, and information on the other signal strength from the image sensor 207, by a one-time inspection, where the two signal strengths are different from each other. Because the signal strength representing the light scattering from the defect is different depending on what wavelength, deflection, and angle of elevation from the inspection are selected for each illumination light beam, it is possible to more precisely extract information on defect classification when the ratio of the signal strength obtained from the image sensor 205 and the signal strength obtained from the image sensor 207 is used as a characteristic amount.

[Sixth Embodiment]

Figure 11:
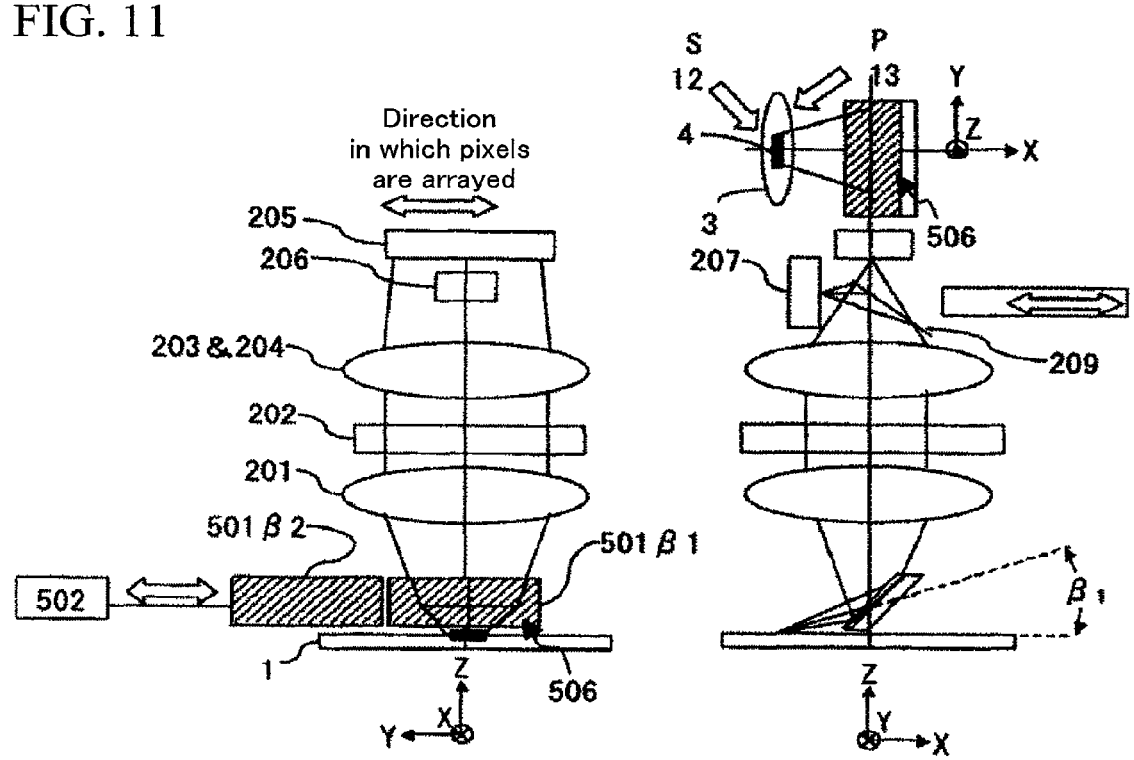
FIG. 11 is a conceptual diagram of a sixth embodiment of the present invention.

Descriptions will be provided for a sixth embodiment of the oblique inspection according to the present invention by use of FIG. 11. An object of the present embodiment is to accomplish a method characterized in that a defect in the detection area 4 of the image sensor is detected by use of two sensors simultaneously in a case where the deflection of the illumination light beam is selected as a condition for the illumination. To this end, it is desirable that the detection area 4 of the image sensor should be irradiated with a P deflected light beam and a S deflected light beam, and that the S deflected light beam and the P deflected light beam whose light paths are branched by use of the reflected-beam splitter 209 should be capable of being detected by the sensor 205 and by the sensor 207. The beam spot 3 is formed in the detection area 4 of an image sensor which is set off the optical axis of the detection lens 201, and which is positioned in parallel to the Y axis. In the case of the present embodiment, the illumination light beam 12 is S deflected light beam, and the illumination light beam 13 is P deflected light beam. Light obtained from the detection area 4 is reflected by the reflecting surface 506 of one of the two plane reflecting mirrors 501, which is selected by the mirror switching mechanism 502. The plane reflecting mirrors 501 are those tilted in order for the angles of elevation for the detection to be equal to $\beta 1$ and $\beta 2$, respectively. After the reflection, the light is caused to enter the detection lens 201. The pattern noise of the resultant light is removed by the spatial filter 202 arranged in the Fourier transform surface of the detection lens 201. The resultant light is formed into an image on the image sensor 205 with a predetermined magnification by the image forming lens 203 and the zoom lens group 204. It is possible to observe the surface of the detection area 4 or the surface of the spatial filter 202 by use of the observation optical system 206. In the case of the present embodiment, the reflected-beam splitter 209 is inserted between the detection optical system 200 and the image sensor, and thereby the light path is branched by the deflected-beam splitter 209 thus inserted so that an image is formed on each of the image sensors 207 and 205.

The foregoing configuration makes each of the signal strengths representing the light scattering from the defect different depending on the deflection direction. For this reason, when the light obtained from the same defect is branched by the reflected-beam splitter 209, the configuration is capable of causing light corresponding to one of the different deflection components to be formed into an image on the image sensor 205 and light corresponding to the other of the different deflection components to be formed into an image on the image sensor 207. This makes it possible to classify the defect on the basis of the signal strength ratio. If the reflected-beam splitter 209 is replaced with an element capable of separating wavelengths, by making the wavelength different between the illumination light beams 12 and 13, it is possible to obtain information on a signal strength corresponding to the illumination light beam 12 and information on the other signal strength corresponding to the illumination light beam 13 simultaneously by a one-time inspection, where the two signal strengths are different from each other. Because each of the signal strengths representing the light scattering from the defect is different depending on what wavelength, deflection, and angle of elevation for the inspection are selected for each illumination light beam, it is possible to more precisely extract information on defect classification when the ratio of the signal strength obtained from the sensor 205 and the signal strength obtained from the sensor 207 is used as a characteristic amount.

[Seventh Embodiment]

Figure 12:
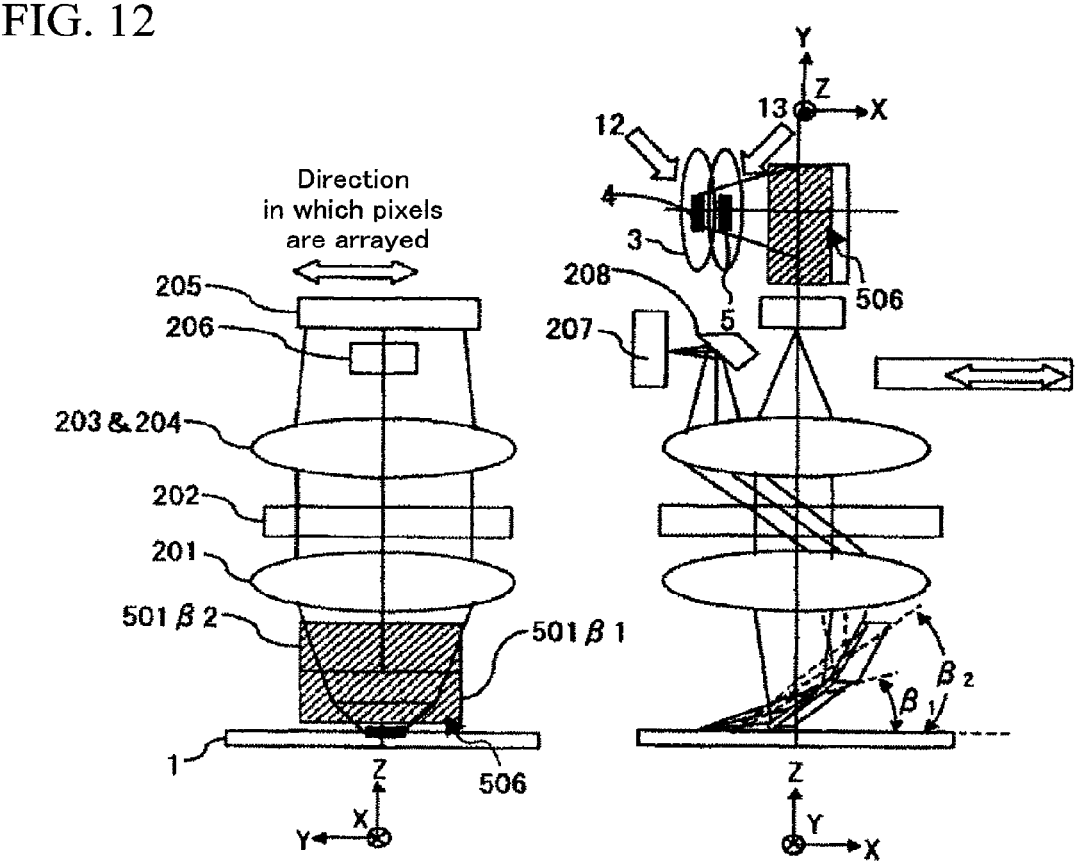
FIG. 12 is a conceptual diagram of a seventh embodiment of the present invention.

Descriptions will be provided for a seventh embodiment of the oblique inspection according to the present invention by use of FIG. 12. An object of the present embodiment is to accomplish a method characterized in that a defect is detected by simultaneous use of two angles of elevations for the illumination. To this end, it is desirable that the two plane reflecting mirrors 501 respectively corresponding to the different angles β1 and β2 should be simultaneously arranged, between the detection lens 201 and the substrate 1, in the light path from the detection area 4 to the detection lens 201 or the light path from the detection area 5 to the detection lens 201. In the case of the present embodiment, by use of the illumination light beam 12, the beam spot 3 is formed in the detection area 4 of an image sensor which is set off the optical axis of the detection lens 201, and which is positioned in parallel to the Y axis. The light obtained from the detection area 4 of the image sensor is caused to enter the detection lens 201 after reflected by the reflecting surface 506 of the plane reflecting mirror 501 tilted so that the angle of elevation for the detection can be equal to β1. After the reflection, the pattern noise of the resultant light is removed by the spatial filter 202 arranged in the Fourier transform surface of the detection lens 201. The resultant light is formed into an image on the image sensor 205 with a predetermined magnification through the image forming lens 203 and the zoom lens group 204. Any one of the detection area 4 and the surface of the spatial filter 202 is capable of being observed by use of the observation optical system 206. On the other hand, by use of the illumination light beam 13, the beam spot 3 is formed in the detection area 5 of an image sensor which is set off the optical axis of the detection lens 201, and which is positioned in parallel to the Y axis. The light obtained from the detection area 5 of the image sensor is caused to enter the detection lens 201 after reflected by the reflecting surface 506 of the plane reflecting mirror 501 tilted so that the angle of elevation for the detection can be equal to β2. The plane reflecting mirror 208 for branching a light path is inserted between the detection optical system 200 and the image sensor, and thus the light path of the light from the detection area 5 is branched by the plane detection mirror 208. As a result, the resultant light is formed into an image on the image sensor 207.

The foregoing configuration causes the light beam obtained from the detection area 4 by use of one of the two different angles and the light beam obtained from the detection area 5 by use of the other of the two different angles to pass the corresponding different positions in the detection optical system 200. For this reason, it is possible to cause the two light beams to be formed into the images on the two image sensors 205 and 207, respectively. This makes it possible to carry out the oblique inspection by simultaneously applying the two angles of elevation to the light obtained from the defect by a one-time inspection. As a result, it is possible to detect the defect with a higher NA, which is more than 0.9 for instance, by combining the inspection from above with the oblique inspection according to the present embodiment. This makes it possible to receive almost all the light scattering from the defect, and accordingly to increase the number of types of detected defects and the number of detected defects. In addition, like the fourth embodiment, by making the wavelength and deflection different between the illumination light beams 12 and 13, the present embodiment makes it possible to obtain information on the signal strength from the image sensor 205 and information on the signal strength from the image sensor 207 by a one-time inspection, where the two signal strengths are different from each other. Because the signal strength representing the light scattering from the defect is different depending on what wavelength, deflection, and angle of elevation for the inspection is selected for each illumination light beam, it is possible to more precisely extract information on defect classification when the ratio of the signal strength obtained from the image sensor 205 and the signal strength obtained from the image sensor 207 is used as a characteristic amount.

[Eighth Embodiment]

Figure 13:
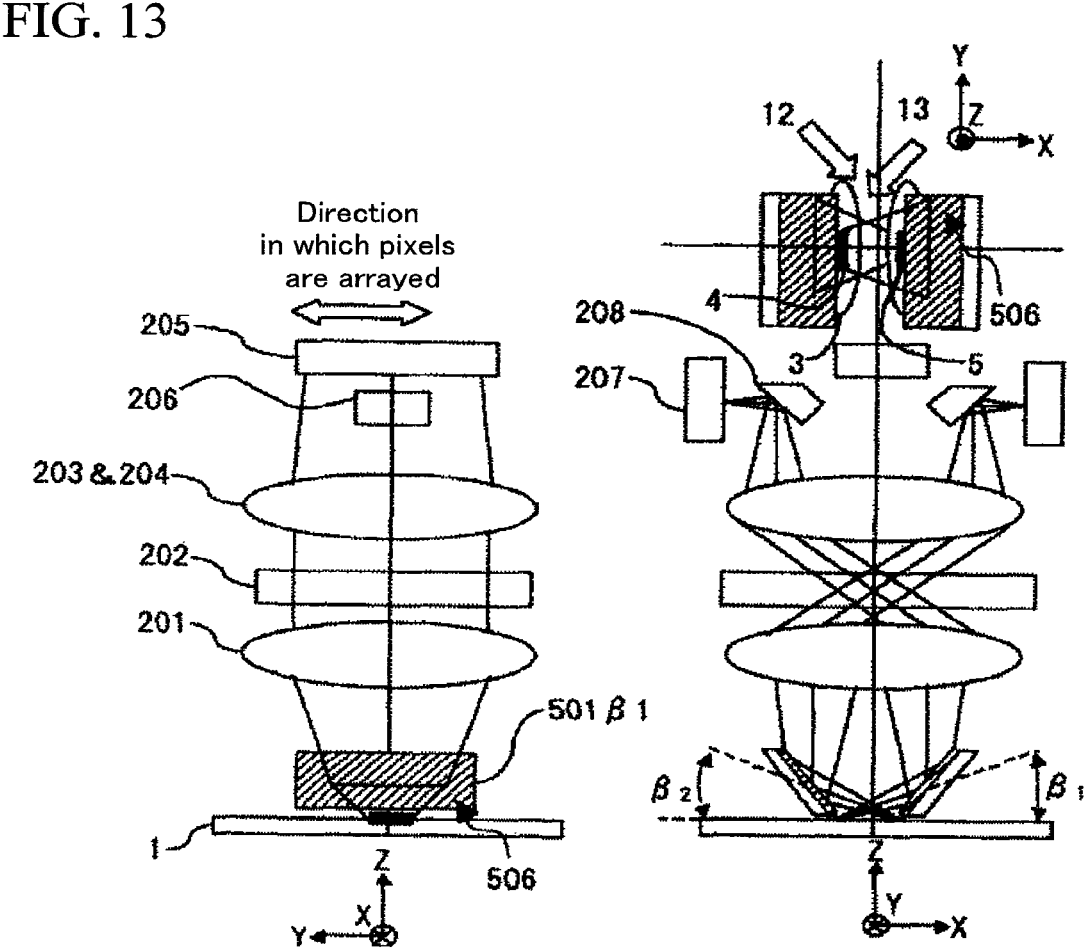
FIG. 13 is a conceptual diagram of an eighth embodiment of the present invention.

Descriptions will be provided for an eighth embodiment of the oblique inspection according to the present invention by use of FIG. 13. An object of the present embodiment is to accomplish a method in which two mechanisms each capable of carrying out an oblique inspection are arranged by shifting their corresponding detection areas in a direction (in the X-axis direction in the case of the present embodiment) perpendicular to a direction (a longitudinal direction) in which the pixels are arrayed in each corresponding one of the image sensors, and which accordingly makes it possible to simultaneously carry out two types of oblique inspection by a one-time inspection. Specifically, it is desirable that two plane reflecting mirrors 501 tilted at their respective different angles (otherwise, at the same angles) should be arranged opposite to each other between the detection lens 201 and the substrate 1, and that the illumination light beams 12 and 13 should be thus irradiated on the respective detection areas 4 and 5 of their image sensors. The light path of scattering light originating from the illumination light beam 12 is bent by one of the two plane reflecting mirrors 501 whereas the light path of scattering light origination from the illumination light beam 13 is bent by the other of the two plane reflecting mirrors 501. Accordingly, the two light paths are different from each other in the detection optical system 200. This enables the scattering light originating from the illumination light beam 12 to be formed into an image on the image sensor 205, and the scattering light originating from the illumination light beam 13 to be formed into an image on the image sensor 207. By use of the illumination light beam 13, the beam spot 3 is formed in the detection area 4 of one of the image sensors, which is set off the optical axis of the detection lens 201, and which is positioned in parallel to the Y axis. Light obtained from the detection area 4 of the image sensor is caused to enter the detection lens 201 after reflected by the reflecting mirror 506 of the plane reflecting mirror 501 tilted so that the angle of elevation for the inspection can be equal to β1. On the other hand, by use of the illumination light beam 12, the beam spot 3 is formed in the detection area 5 of the other of the image sensors, which is set off the optical axis of the detection lens 201, and which is positioned in parallel to the Y axis. Light obtained from the detection area 5 of the image sensor is caused to enter the detection lens 201 after reflected by the reflecting surface 506 of the plane reflecting mirror 501 tilted so that the angle of elevation for the inspection can be equal to β2. After passing the detection optical system 200, each of the light paths of the two light beams from the plane reflecting mirrors 501 are branched by each of the plane reflecting mirrors 208 each for branching a light path, which are inserted between the detection optical system 200 and the image sensors, and thereby are formed into images respectively on the image sensors 207.

In addition, by placing the plane reflecting mirrors 501 in and out by use of the switching mechanism 502 (see FIG. 6), it is possible to carry out the inspection from above in which an image is formed on the image sensor 205. The pattern noise of the light is removed by the spatial filter 202 arranged in the Fourier transform surface of the detection lens 201. The resultant light is formed into an image on the image sensor 205 with a predetermined magnification through the image forming lens 203 and the zoom lens group 204. The detection areas and the surface of the spatial filter 202 can be observed by use of the observation optical system 206.

Like the fourth embodiment, too, by making the wavelength and deflection different between the illumination light beams 12 and 13, the present embodiment makes it possible to simultaneously obtain information on a signal strength obtained from one of the two image sensors 207 and information on a signal strength obtained from the other of the two image sensors 207 by a one-time inspection, where the signal strengths are different from each other. Because the signal strength of the light scattering from the defect is different depending on what wavelength, deflection, and angle of elevation for the inspection are selected for each illumination light beam, it is possible to more precisely extract information on defect classification when the ratio of the signal strength obtained from one of the two image sensors 207 and the signal strength obtained from the other of the two image sensors 207 is used as a characteristic amount.

[Ninth Embodiment]

Figure 14:
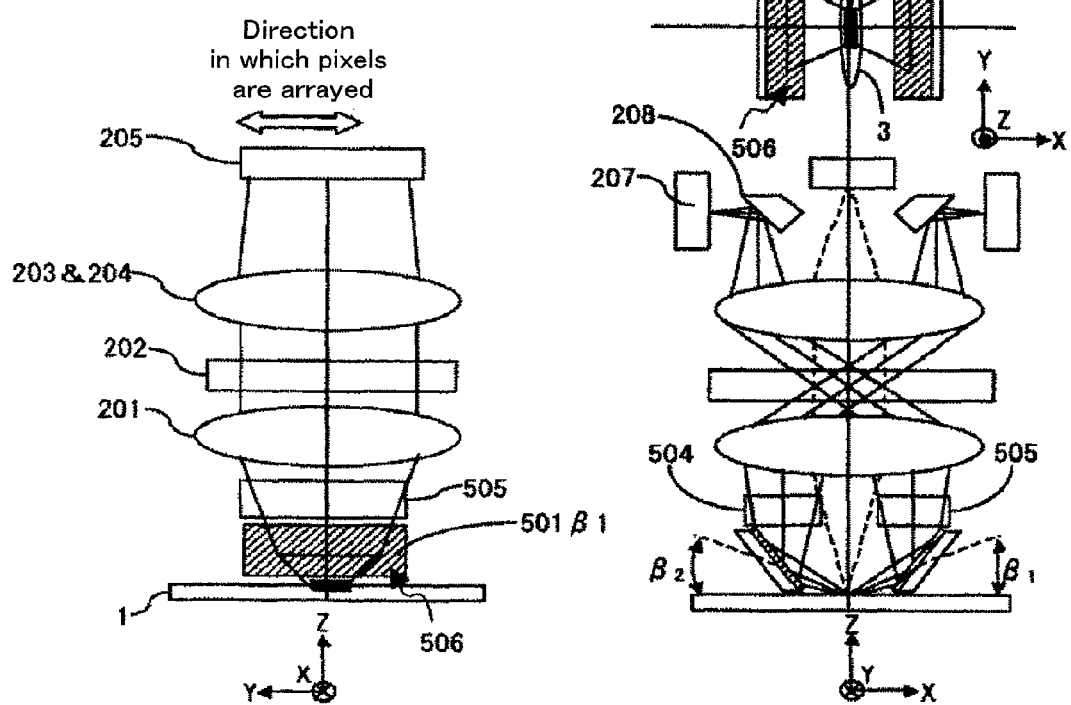
FIG. 14 is a conceptual diagram of a ninth embodiment of the present invention.

Descriptions will be provided for a ninth embodiment of the oblique inspection according to the present invention by use of FIG. 14. An object of the present embodiment is to accomplish a method in which two mechanisms each capable of carrying out an oblique inspection are arranged opposite to each other, and which makes it possible to carry out three types of inspection, by a one-time inspection, the three types of inspection including two types of oblique inspection using these two image sensors each for the oblique inspection and an inspection from above using the image sensor for the inspection from above.

To this end, it is desirable that two plane reflecting mirrors 501 titled at their different angles (otherwise, at the same angle) should be arranged opposite to each other between the detection lens 201 and the substrate 1, and that the beam spot 3 should be formed in the detection area 6 of each of the image sensors which are arranged at positions each in parallel to the Y axis on the optical axis of the detection lens 201 by irradiating the detection area 6 of each of the image sensors with the illumination light beams 12 and 13. The light path of scattering light originating from the illumination light beam 12 is bent by one of the two plane reflecting mirrors 501 whereas the light path of scattering light originating from the illumination light beam 13 is bent by the other of the two plane reflecting mirrors 501. Accordingly, the two light paths are different from each other in the detection optical system 200. As a result, this enables the scattering light originating from each of the illumination light beams 12 and 13 to be formed into an image on each corresponding one of the image sensors 207 for the oblique inspection as well as on the image sensor 205 for the inspection from above. Thereby, it is possible to create three light paths for the inspection, and accordingly to carry out the two types of oblique inspection and the inspection from above simultaneously by a one-time inspection.

With regard to a first light path, light obtained from the detection area 6 of one of the image sensors for the oblique inspection is caused to enter the detection lens 201 after reflected by the reflecting surface 506 of the plane reflecting mirror 501 tilted so that the angle of elevation for the inspection can be equal to β1. The pattern noise of the resultant light is removed by the spatial filter 202 arranged in the Fourier transform surface of the detection lens 201. Thus, the resultant light is formed into an image on the image sensor 205 with a predetermined magnification through the image forming lens 203 and the zoom lens group 204. The detection area 6 and the surface of the spatial filter 202 can be observed by use of the observation optical system 206. With regard to a second light path, the light obtained from the detection area 6 of the other of the image sensors for the oblique inspection is caused to enter the detection lens 201 after reflected by the reflecting surface 506 of the plane reflecting mirror 501 tilted so that the angle of elevation for the inspection can be equal to β2. With regard to a third light path, the light from the detection area 6 of the image sensor for the inspecting from above is caused to enter the detection lens 201 directly. After passing the detection optical system 200, the first and second light paths are formed into the images respectively on the different image sensors 207 by the plane reflecting mirrors 208 each for branching a light path, which are each inserted between the detection optical system 200 and the image sensors. The third light path is directly formed into the image on the image sensor 205 through the detection optical system 200. In addition, it is possible to obtain correct focus of each of the three light paths for the detection in terms of an object point by arranging the lens-type light path length correcting elements 504 and 505 between the detection lens 201 and the plane reflecting mirrors 501. This makes it possible to obtain a correct magnification in the Y-axis direction. Like the fourth embodiment, by making the wavelength and deflection different between the illumination light beams 12 and 13, the present embodiment makes it possible to simultaneously obtain information on a signal strength from the image sensor 205 and information on a signal strength from each of the image sensors 207 by a one-time inspection, where the three signal strengths are different from one another. Because the signal strength of the light scattering from the defect is different depending on what wavelength, deflection, and angle of elevation for the inspection are selected for each of the illumination light beams 12 and 13, it is possible to more precisely extract information on defect classification when the ratio among the signal strengths obtained from the three sensors is used as a characteristic amount.

[Tenth Embodiment]

Figure 15:
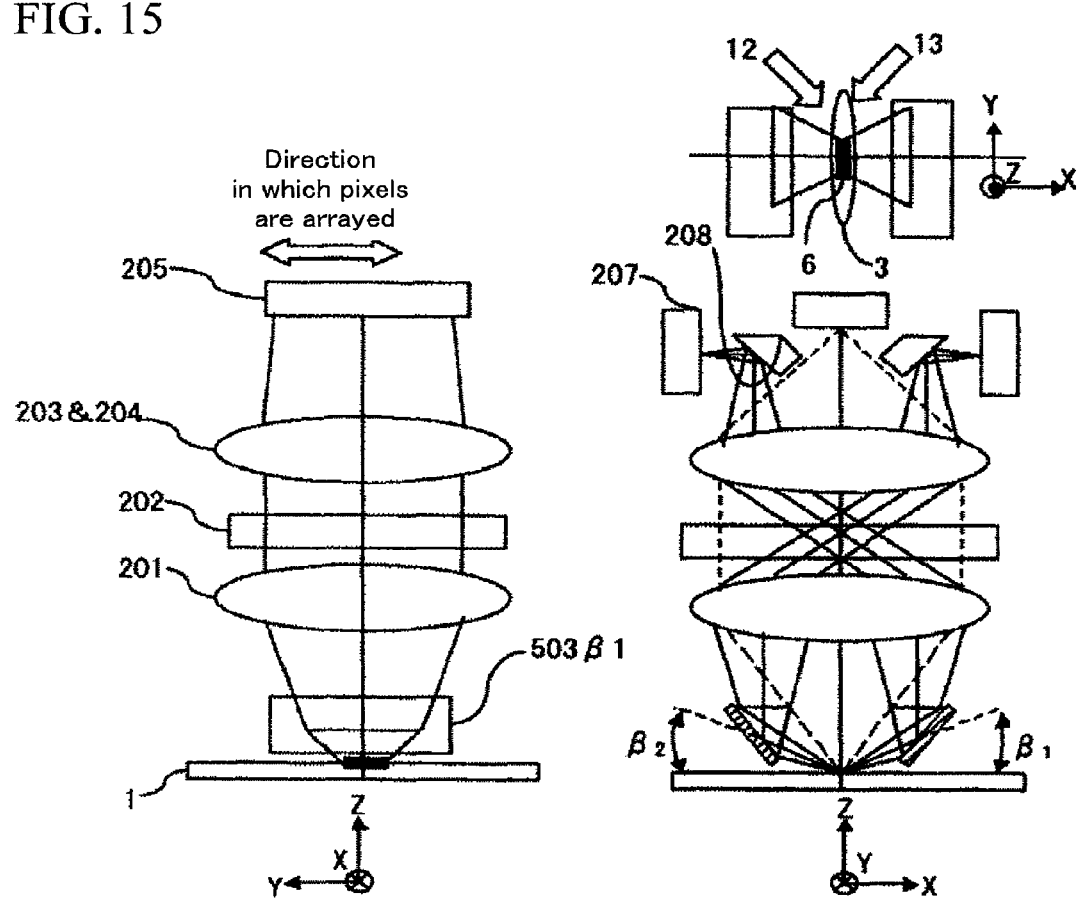
FIG. 15 is a conceptual diagram of a tenth embodiment of the present invention.

Descriptions will be provided for a tenth embodiment of the oblique inspection according to the present invention by use of FIG. 15. The present embodiment is the same as the ninth embodiment, except that the oblique inspection is carried out by use of prism-type plane reflecting mirrors. Specifically, the illumination light beams 12 and 13 are irradiated on the detection area 6 of each of the image sensors located at positions each in parallel to the Y axis on the optical axis of the detection lens 201, and thus the beam spot 3 is formed on the detection area 6. With regard to a first light path, light obtained from the detection area 6 of one of the image sensors, which is irradiated with the illumination light beam 13, is caused to enter the detection lens 201 after reflected by the reflecting surface of one of the prism-type light path length correcting elements 503, which is tilted so that the angle of elevation can be equal to $\beta 1$. With regard to a second light path, light obtained from the detection area 6 of the other of the image sensors, which is irradiated with the illumination light beam 12, is caused to enter the detection lens 201 after reflected by the reflecting surface of the other of the prism-type light path length correcting elements 503, which is tilted so that the angle of elevation can be equal to $\beta 2$. With regard to a third light path, light from the detection area 6 of the image sensor is caused to enter the detection lens 201 directly. By arranging the light path length correcting elements 503 between the detection lens 201 and the substrate 1, it is possible to bring each of the light paths into focus in terms of the object point, and accordingly to obtain a correct magnification in the Y-axis direction. After passing the detection optical system 200, the first and second light paths are formed into images on the corresponding image sensors 207 by the plane reflecting mirrors 208 each for branching a light path, which are inserted between the detection optical system 200 and the image sensors. In addition, the third light path is directly formed into an image on the image sensor 205 through the detection optical system 200. The pattern noise of the light is removed by the spatial filter 202 arranged in the Fourier transform surface of the detection lens 201. The resultant light is formed into the image on the image sensor 205 with a predetermined magnification through the image forming lens 203 and the zoom lens group 204. Furthermore, the detection areas 6 and the surface of the spatial filter 202 can be observed by use of the observation optical system 206.

Like the configuration according to the fourth embodiment, by making the wavelength and deflection between the illumination light beams 12 and 13 for the inspection, the configuration according to the present embodiment makes it possible to simultaneously obtain information on a signal strength from the image sensor 205 and information on a signal strength from each of the image sensors 207 by a one-time inspection, where the three signal strengths are different from one another. Because the signal strength representing the light scattering from the defect is different depending on what wavelength, deflection, and angle of elevation for the inspection are selected for each of the illumination light beams, it is possible to more precisely extract information on defect classification when the ratio among the signal strengths each obtained from the image sensor 205 and the two image sensors 207 is used as a characteristic amount.

Figure 16:
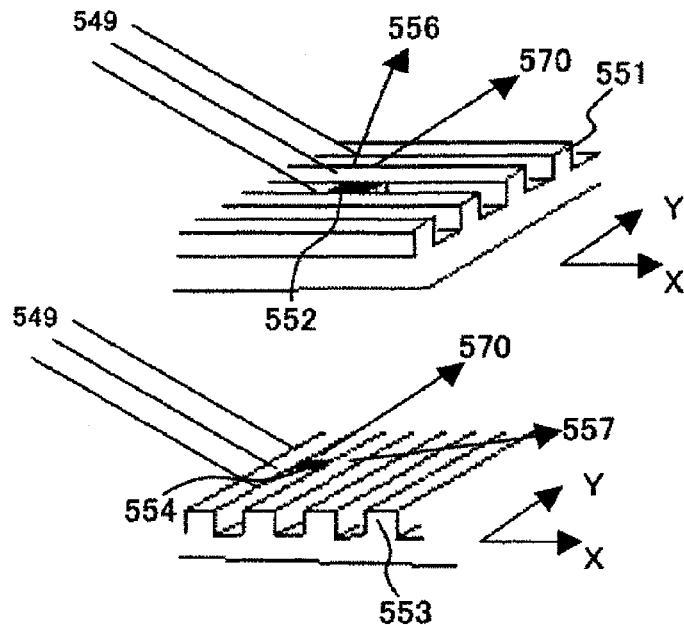
FIG. 16 is a model diagram showing a pattern, a defect, and a direction in which light scatters from the defect.

At this point, by use of FIG. 16, detailed descriptions will be provided for patterns formed on the substrate 1 and defects existing on the same substrate 1 which are intended to be detected by use of the defect inspection apparatuses according to the embodiments.

The pattern is formed on the substrate 1 in the X-axis and Y-axis directions, which are orthogonal to each other. FIG. 16 shows a linear pattern 553 formed in the Y-axis direction and a linear pattern 551 formed in the X-axis direction. In general, patterns are formed through exposure, development, and etching processes. For example, a short-circuit defect which occurs due to variation and the like in process conditions when an exposure process is performed out of focus may lie in the shortest distance between interconnections in some cases. An example of a short-circuit defect in the pattern 553 formed in the Y-axis direction is shown as a defect 554 existing between two adjacent interconnections in the X-axis direction, and an example of a short-circuit defect in the pattern 551 formed in the X-axis direction is shown as a defect 552 existing between two adjacent interconnections in the Y-axis direction. In a case where the defects 552 and 554 are illuminated obliquely with the Y-Z plane assigned as the surface of incidence for the purpose of inspecting the defects 552 and 554, this oblique illumination is an illumination in parallel to the pattern 551, and is an illumination orthogonal to the pattern 553. In this case, the defect 552 existing in the pattern 551 in parallel to the illumination light beam 549 can secure a sufficient area for the scattering, whereas the defect 554 existing in the pattern 553 orthogonal to the same illumination light beam receives an insufficient amount of illumination because the defect 554 is shadowed by the pattern 553. As a result, the amount of light scattering from the defect 554 is reduced. This makes it difficult to detect the defect 554. By contrast, in a case where the surface of incidence is tilted to the Y-Z plane, the defect 554 is less shadowed by the pattern 553 when viewed from the azimuth of illumination. This increases the amount of illumination light entering the defect 554. Thereby, the amount of light scattering from the defect 554 is increased. This makes it easier to detect the defect 554. In a case where the surface of incidence is tilted to both the Y-Z plane and the X-Z plane, the illumination light 549 causes scattering light ray 556 from the pattern 551 formed in the X-axis direction, scattering light ray 570 from the defects 552 and 554, and scattering light ray 557 from the pattern 553 formed in the Y-axis direction. The scattering light rays 556, 557 and 570 are specular reflections.

The tilting of the azimuth of illumination to the X axis and the Y axis in this manner makes it easier to detect the short-circuit defect or the like existing between two adjacent interconnections. Also, an angle of elevation for illumination changes an easy-to-detect defective shape of a convex defect such as a foreign matter, a concave defect such as a scratch, or the like. For this reason, it is desirable that the defect inspection apparatuses should have a mechanism enabling not only the azimuth of illumination but also the angle of elevation for the illumination to be adjusted in order that a condition for maximizing S/N (signal to noise ratio) for the inspection can be selected depending on the shape of a pattern formed on a substrate to be inspected and the shape of a pattern as an inspection object.

Figure 17:
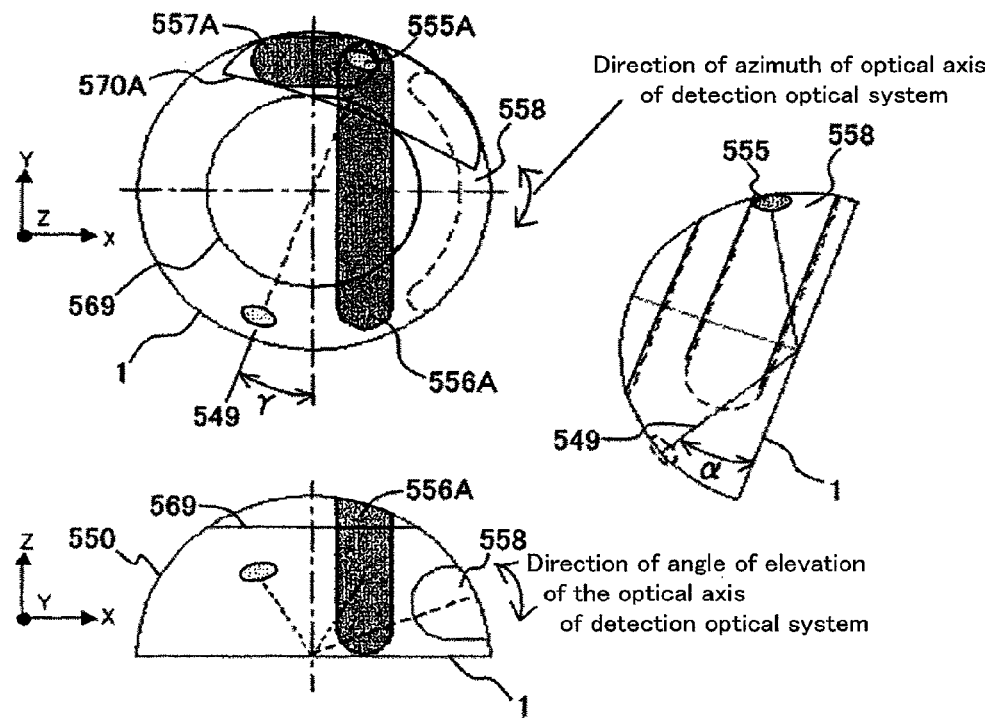
FIG. 17 is a diagram showing a relationship between an azimuth at which a detection optical system detects light scattering from a defect and an azimuth at which the defect is illuminated.

FIG. 17 shows a relationship between an azimuth at which light scattering from a defect is detected by use of the detection optical system 200 and an azimuth at which the defect is illuminated. Assume that, as shown in FIG. 17, a hemisphere 550 exists about the center of a beam spot formed on the substrate 1 by use of the illumination light beam 549 (the center is the origin of the hemisphere). FIG. 17 shows a plan view (the X-Y plane) of the assumed hemisphere 550, a side view (the X-Z plane) of the assumed hemisphere 550 when viewed in the Y-axis direction, and a side view of the assumed hemisphere 550 when viewed in a direction orthogonal to an azimuth at which the substrate 1 is illuminated with the illumination light beam 549. The light rays (specular reflections) 556, 557 and 570 (see FIG. 16) scattering from the defect and the pattern spread hemispherically. As a result, the light rays 556, 557 and 570 respectively enter areas 556A, 557A and 570A on the assumed hemisphere 550, as shown in FIG. 17. In FIG. 17, reference numeral 569 denotes a projection of an opening of the system for the detection from above on the hemisphere 550. The azimuth at which the substrate 1 is illuminated with the illumination light beam 549 (or the surface of incidence) is tilted to the Y-Z plane at an angle of γ. As shown in FIG. 17, the specular reflection from a horizontal flat part on the substrate 1 enters an area 555A which is symmetrical therewith with respect to a line (the Z axis) from the apex of the assumed hemisphere 550 to the origin thereof. An area 556A which light ray 556 scattering from the pattern enters and an area 557A which light ray 557 scattering from the pattern enters shift depending on the angle γ of the illumination light beam 549 for the inspection and the angle α of elevation.

Assume that normal patterns exist in both the X-axis direction and the Y-axis direction. The specular reflection 556 from the pattern 551 extending in the X-axis direction as shown in FIG. 16 gathers chiefly in the area 556A, which includes the area 555A which the specular reflection coming from the flat part enters. This area 556A extends in the Y-axis direction. In addition, the specular reflection 557 from the pattern 553 extending in the Y-axis direction gathers in the area 557A, which includes the area 555A which the specular reflection coming from the flat part enters. This area 557A extends in the X-axis direction. By contrast, the specular reflection 570 coming from the defect having a shape different from the patterns enters the area 570A which is different from the specular reflections 556 and 557 coming from the respective patterns. This area 570A overlaps the area 555A, and overlaps parts or all of the areas 556A and 557A, depending on the angle γ of the illumination light beam 549. FIG. 17 illustratively shows what happens in a case where the strength of the forward scattering light of the specular reflection 570 coming from the defect is strong.

The detection optical system 200 and the plane reflecting mirror 501 are arranged in this defect inspection apparatus so as to detect only the light scattering from the defect, or so as to capture the scattering light 570 entering the area which does not overlap the area 556A which the light 556 scattering from the normal pattern is likely to enter or the area 557A which the light 557 scattering from the normal pattern is likely to enter. As shown in FIG. 17, for example, the detection optical system is arranged so that the opening 558 projected on the assumed hemisphere 550 should overlap only the area 570A, but not the area 566A or the area 557A. The area of the opening 558 overlapping only the area 570A varies depending on how large the angle γ of the illumination light beam 549 for the inspection is, and how the opening 558 of the detection optical system is set up. For this reason, it is desirable that the angle γ and the opening 558 should be set up in terms of their arrangement and size so that the area of the opening 558 overlapping only the area 570 can be as large as possible.

NA (the numerical aperture) of the detection optical system in the direction of the angle of elevation (along the X-Z plane) is limited to a range in which the light rays 556 and 557 scattering from each of the patterns are prevented from entering. For this reason, the opening 558 needs to be enlarged in the direction of the azimuth from the optical axis of the detection optical system for the purpose of increasing the amount of scattering light to be captured, and this enlargement is effective for efficiently capturing only the light ray 570 scattering from the defect.

Because of its configuration, heretofore, it is difficult to increase NA of the detection optical system used with a low angle of elevation. In the case of the embodiments of the present invention, NA of the detection optical system can be increased up to NA of the detection lens, or up to the full opening (for example, NA=0.6, NA=0.8, or the like), in the direction of the azimuth of the optical axis thereof by limiting the opening 558 of the detection optical system in the direction of the angle of elevation. When the defect inspection apparatus has the configuration which causes the plane reflecting mirror to bend the optical axis thereof as in the case of the defect inspection apparatuses according to the foregoing embodiments, it is possible to increase NA of the detection optical system corresponding to the opening 558 up to NA of the detection lens in the direction in which the pixels are arrayed in the image sensor. This makes it possible to increase the amount of light scattering from the defect, which is captured by the detection optical system, and to hold low the amount of light scattering from the normal patterns, which is captured by the detection optical system. For this reason, it is possible to increase S/N for the inspection.

The setting up of the opening so that the value of NA of the detection optical system in the direction of the angle of elevation from the optical axis thereof should be different from the value of NA of the detection optical system in the horizontal direction is not necessarily limited to the scheme in which the mirror is used, but is applicable to a configuration in which another detection lens is additionally provided thereto. An example of such a configuration is shown in the following eleventh embodiment.

[Eleventh Embodiment]

Figure 20:
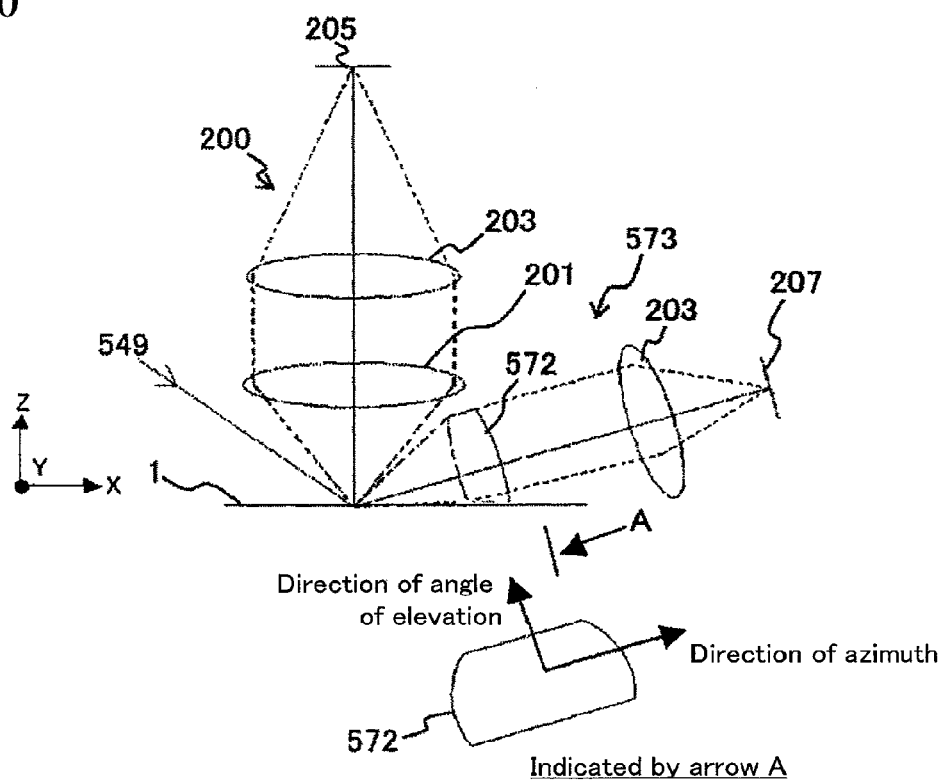
FIG. 20 is a conceptual diagram of oblique inspection according to an eleventh embodiment of the present invention.

FIG. 20 is a conceptual diagram of the eleventh embodiment of the oblique inspection according to the present invention. In addition to the foregoing detection optical system 200, a low-elevation-angle detection optical system 573 for the oblique inspection is arranged in the defect inspection apparatus according to the present embodiment. The low-elevation-angle detection optical system 573 has almost the same configuration as the detection optical system 200 has. However, a spatial restriction is imposed on a detection lens (an objective lens) 572 of the low-elevation angle detection optical system 573 by the substrate 1 from below and the detection optical system 200 from above. For this reason, the detection lens 572 has a shape which limits the opening in the direction of the angle of elevation from the optical axis by removing upper and lower portions of the detection lens 572 as indicated by an arrow A in FIG. 18. The low-elevation-angle detection optical system 573 may have this kind of configuration.

[Twelfth Embodiment]

Figure 18:
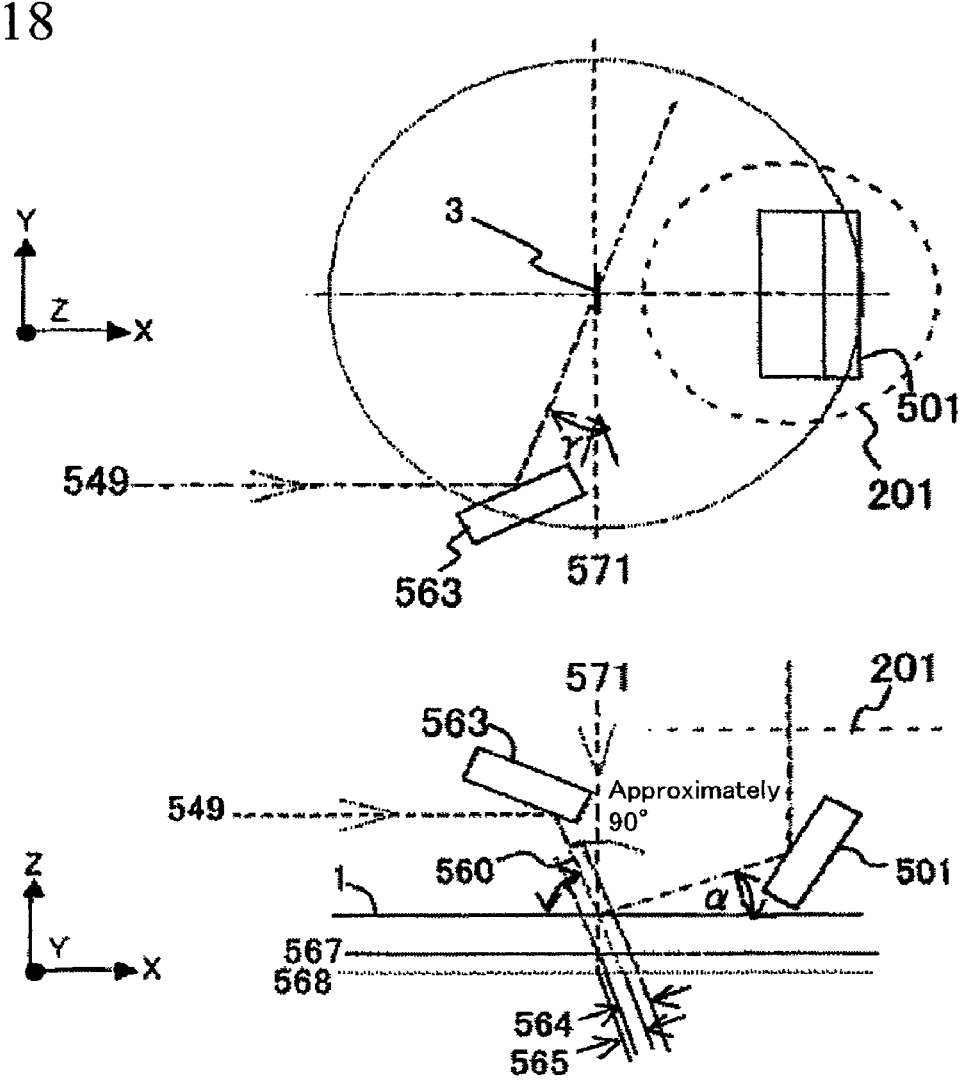
FIG. 18 is a conceptual diagram of oblique inspection according to a twelfth embodiment of the present invention.

FIG. 18 is a conceptual diagram of a twelfth embodiment of the oblique inspection according to the present invention. The present embodiment shows how the illumination optical system is optimally laid out relative to the detection optical system for the oblique inspection. In the case of the present embodiment, the illumination optical system is provided with an illumination mirror 563 for reflecting and thus bending the illumination light beam irradiated thereon. As shown in the plane view of FIG. 18, when viewed from above, the illumination light beam 549 irradiated from the illumination optical system is bent by the illumination mirror 563, and the illumination light beam 549 thus reflected is formed into the beam spot 3 on the substrate 1 at an azimuth tilted to the Y axis by the angle γ. As in the case of the detection optical system according to the first embodiment, the detection optical system according to the present embodiment has the plane reflecting mirror 501 and the detection lens 201 which are arranged on the X axis, and thus captures the light scattering from the defect. When viewed from the side (in the Y-axis direction), the illumination light beam 549 is bent by the illumination mirror 563, and is thus irradiated on the substrate 1 at the angle α of elevation for the illumination which forms approximately 90° with the angle β of elevation of the detection optical system 200.

In the case of this configuration, the illumination mirror 563 is arranged so that the angle between the plane including the optical axis of the luminous flux of the illumination light beam and the longitudinal axis (the Y axis) of the beam spot 3, and the optical axis of the luminous flux of the scattering light which enters the detection optical system 200 can be approximately 90°. This makes it possible to obtain the correct focus even if the height of the substrate 1 changes. When the height of the substrate 1 changes, the position of the beam spot 3 which is formed on the substrate 1 by the illumination light beam 549 moves along a focus plane 560 which brings the detection optical system 200 into focus. This is because the plane including the optical axis of the luminous flux of the illumination light beam and the longitudinal axis of the beam spot 3 is equal to the focus plane 560, and because the optical axis of the illumination light beam 549 exists on the focus plane 560 after reflected by the illumination mirror 563. The beam spot 3 always exists on the focus plane 560 in this manner. For this reason, as long as the detection optical system 200 is brought into focus on the beam spot 3, the detection optical system 200 is kept in the state in which the detection optical system 200 is in focus on the beam spot 3 which is formed by the illumination light beam 549, regardless of the height of the substrate 1.

An illumination at another angle of elevation, for example, an illumination 571 from the Y-Z plane is formed into a beam spot on the nodal line between the Y-Z plane and the substrate 1. As a result, the beam spot moves along the Y-Z plane as the substrate 1 moves upward and downward. This makes it likely that the beam spot formed by the illumination light beam 571 may be out of the depth of focus 564 of the detection optical system 200. For example, when the substrate 1 is lowered to a height 568, the beam spot formed by the illumination light beam 571 is out of the depth of focus 564. As a result, the beam spot is out of focus by an amount 565 due to the scattering light originating from the illumination light beam 571. FIG. 17 shows an example in which the beam spot formed by the illumination light beam 571 is out of the depth of focus 564 when the substrate 1 is placed at a position lower than the height 567.

Figure 19:
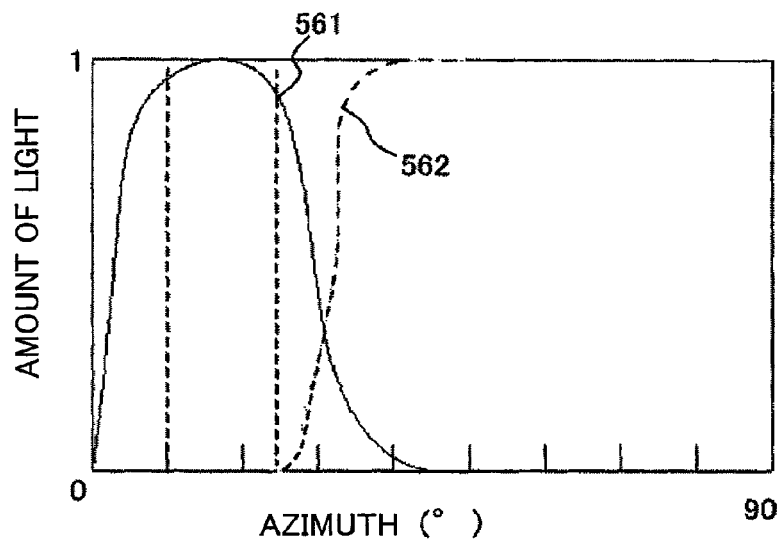
FIG. 19 is an explanatory diagram illustrating an appropriate range of an illuminating azimuth γ in the twelfth embodiment.

Descriptions will be provided for what is a range appropriate for the azimuth γ for the illumination in the twelfth embodiment by use of FIG. 19.

Because the angle between the plane including the optical axis of the luminous flux of the illumination light beam and the longitudinal axis of the beam spot 3, and the optical axis of the detection optical system is approximately 90° in the foregoing side view, the azimuth γ for the illumination can be converted from the following equation $$\sin \gamma = \tan \alpha \cdot \tan \beta \quad \text{(Equation 1)}$$

where α is the angle of elevation of the plane including the optical axis of the luminous flux of the illumination light beam and the longitudinal axis of the beam spot 3, and β is the low angle of elevation of the detection optical system.

A profile 561 shown in FIG. 19 represents the distribution of the amount of the scattering light which is captured by the detection optical system for the oblique detection when the angle of elevation for the detection is β. This distribution of the amount of the scattering light is shown by converting the angle β of elevation for the detection to the azimuth γ for the illumination by use of Equation 1. On the other hand, a profile 562 shown there represents the distribution of the amount of the light scattering the patterns, which is captured by the detection optical system for the oblique detection when the azimuth for the illumination is γ. In addition, the angle β of elevation for the detection needs to be set up in a range where γ>approximately 10° when converting the angle β of elevation for the detection to the azimuth γ for illumination because of a spatial restriction imposed on the mounting. Furthermore, the angle β of elevation for the detection is limited to a range where γ<approximately 25° when converting the angle β of elevation for the detection to the azimuth γ for illumination, on the basis of the profiles 561 and 562 shown in FIG. 19 in order that the angle β of elevation for the detection should not be influenced by the light scattering from the patterns. As a result, it is desirable that the azimuth γ for the illumination should be set at, or approximate to, 17.5° which is the central value between 10° and 25°.

The foregoing descriptions have been provided the embodiments of the present invention. The present invention can be further modified within the scope of its technical thoughts.

What is claimed is:

1. A defect inspection apparatus comprising:
   a stage that is movable relative to an optical system;
   an illumination system for illuminating an inspection area that is situated on the stage;
   a reflecting mirror that reflects light which is scattered from the inspection area;
   an image sensor for converting, to a signal, an image which is formed on the image sensor; and
   a plurality of lenses situated in an optical path that extends from said inspection area to said image sensor, for receiving said light scattered from the inspection area, guiding said light to said image sensor, and forming an image on, said image sensor;
   a signal processing system for processing the signal converted by the image sensor, and thereby detecting defects; wherein
   said reflecting mirror is positioned between said inspection area and a first one of said plurality of lenses that is nearest said inspection area of all lenses that are situated in said optical path;
   a reflecting surface of the reflecting mirror is arranged substantially parallel to a direction in which pixels are arrayed in the image sensor; and
   said reflecting surface is tilted relative to said optical path.

2. A defect inspection apparatus comprising:
   a stage that is movable relative to an optical system;
   a substrate that is to be inspected mounted on the stage;
   an illumination system for illuminating an inspection area on the substrate;
   an optical element comprising a reflecting mirror that reflects light which emanates from the inspection area on the substrate;
   a detection optical system arranged behind said optical element, for detecting light from the inspection area in the substrate;
   a forming optical system which is arranged behind said detection optical system;
   an image sensor for converting, to a signal, an image which is formed on the image sensor by the detection optical system; and
   a signal processing system for processing the signal thus converted by the image sensor, and thus detecting defects; wherein:
   the reflecting mirror is configured to be moved in and out of the light path by a switching mechanism;
   the reflecting mirror forms a detection optical system for oblique inspection with the reflecting mirror in the light path, and a detection optical system for inspection from above with the reflecting mirror out of the light path; and either of oblique inspection and inspection from above is selectable.

3. The defect inspection apparatus according to claim 2, further comprising a plurality of reflecting mirrors whose reflecting surfaces are different from one another in angle.

4. The defect inspection apparatus according to claim 1, further comprising a light-path length correcting element arranged between the reflecting mirror and said first one of said plurality of lenses, wherein:

the light-path length correcting element extends the length of a light path between the inspection area on the substrate and said first one of said lenses, so that oblique inspection can be carried out with the stage positioned at least substantially as high as the stage for the inspection from above; and the light path length correcting element comprises a prismatic light transmitting element.

5. The defect inspection apparatus according to claim 1, further comprising a light-path length correcting element including an image-forming aberration correcting function, the element being arranged between said reflecting mirror and said first one of said lenses.

6. The defect inspecting apparatus according to claim 1, further comprising:

a light path branching reflecting mirror for branching light coming from a reflecting mirror after originating out of the detection optical system; and an oblique inspection image sensor for converting, to a signal, light obtained by branching the light by use of the light path branching reflecting mirror.

7. The defect inspection apparatus according to claim 6, wherein the light path branching reflecting mirror is arranged out of the light path used for the inspection from above.

8. The defect inspection apparatus according to claim 1, wherein an angle between a plane including an optical axis of an illuminating light beam and a longitudinal axis of a beam spot, and the optical axis of light entering the reflecting mirror from the beam spot is set at approximately 90°.

9. The defect inspection apparatus according to claim 8, wherein an illumination direction is set based on a distribution of an amount of scattered light which is acquired by the plurality of lenses and a distribution of an amount of patterned light scattered due to defects, which is acquired by the plurality of lenses.

10. The defect inspection apparatus according to claim 1, wherein the size of the optical system can be expanded in a direction parallel to the substrate, such that light which satisfies a numerical aperture of the detection optical system can be acquired.

11. The defect inspection apparatus according to claim 1, wherein said first one of said plurality of lenses is focused on said inspection area.

* * * * *